(12) United States Patent
Vind et al.

(10) Patent No.: US 8,679,813 B2
(45) Date of Patent: *Mar. 25, 2014

(54) POLYPEPTIDES HAVING LIPASE ACTIVITY AND POLYNUCLEOTIDES ENCODING SAME

(75) Inventors: Jesper Vind, Vaerloese (DK); Kim Borch, Birkeroed (DK); Mikael Mikkelsen, Smorum (DK); Jurgen Carsten Franz Knotzel, Copenhagen (DK)

(73) Assignee: Novozymes A/S, Bagsvaerd (DK)

(*) Notice: Subject to any disclaimer, the term of this patent is extended or adjusted under 35 U.S.C. 154(b) by 160 days.

This patent is subject to a terminal disclaimer.

(21) Appl. No.: 12/762,586

(22) Filed: Apr. 19, 2010

(65) Prior Publication Data

US 2010/0227375 A1 Sep. 9, 2010

Related U.S. Application Data

(63) Continuation of application No. 12/161,083, filed as application No. PCT/US2007/060825 on Jan. 22, 2007, now abandoned.

(60) Provisional application No. 60/761,106, filed on Jan. 23, 2006.

(51) Int. Cl.
| | |
|---|---|
| *C12N 9/20* | (2006.01) |
| *C12P 21/06* | (2006.01) |
| *C12P 19/34* | (2006.01) |
| *C12N 15/00* | (2006.01) |
| *C12N 1/20* | (2006.01) |
| *C07H 21/04* | (2006.01) |
| *C07K 1/00* | (2006.01) |

(52) U.S. Cl.
USPC ...... 435/198; 435/69.1; 435/91.1; 435/320.1; 435/252.3; 536/23.1; 536/23.2; 530/350

(58) Field of Classification Search
USPC ............ 435/198, 69.1, 91.1, 320.1, 252.3; 536/23.1, 23.2; 530/350
See application file for complete search history.

(56) References Cited

U.S. PATENT DOCUMENTS

| 5,705,358 | A | 1/1998 | Gouka et al. |
| 5,869,438 | A | 2/1999 | Svendsen et al. |
| 6,495,357 | B1 | 12/2002 | Fuglsang et al. |
| 7,790,666 | B2 * | 9/2010 | Souter et al. ............... 510/419 |
| 8,187,854 | B2 * | 5/2012 | Vind et al. ................. 435/198 |
| 2004/0053360 | A1 | 3/2004 | Munk et al. |

FOREIGN PATENT DOCUMENTS

| EP | 0 258 068 | 3/1988 |
| EP | 0 305 216 | 3/1989 |
| WO | 93/12237 | 6/1993 |
| WO | WO 97/04079 | 2/1997 |
| WO | WO 00/32758 | 6/2000 |
| WO | 00/60063 A1 | 10/2000 |
| WO | WO 00/60063 | 10/2000 |
| WO | WO 02/062973 | 8/2002 |

OTHER PUBLICATIONS

Derewenda et al., Journal of Lipid Research, vol. 35, pp. 524-534 (1994).
Uniprot Database, Accession No. 059952 (1998).
Broun et al, Science, vol. 282. pp. 1315-1317 (1998).
Devos et al., Structure, vol. 41, pp. 98-107 (2000).
Kisselev et al., Structure, vol. 10, pp. 8-9 (2002).
Seffernick et al., J. Bacteriol., vol. 183, (8), pp. 2405-2410 (2001).
Whisstock et al, Quarterly Review Biophysics, vol. 36, (3), pp. 307-340 (2003).
Wishart et al, J. Biol. Chem., vol. 270, (45), pp. 26782-26785 (1995).
Witkowski et al., Biochemistry, vol. 38, pp. 11643-11650 (1999).
Danielsen et al, Gene, vol. 272, pp. 267-274 (2001).
Hedin et al, Biochem, vol. 44, pp. 16658-16671 (2005).
WO 1993-012237 A1—Geneseq Access No. AAR37878.

* cited by examiner

*Primary Examiner* — Ganapathirama Raghu
(74) *Attorney, Agent, or Firm* — Kristin J. McNamara

(57) ABSTRACT

The present invention relates to polypeptide having lipase activity and which further has a RP of at least 0.8 and a BR of at least 1.1 at the test conditions given in the specification.

26 Claims, 3 Drawing Sheets

```
ID NO 1:     SSSSTQDYRIASEAEIKAHTFYTALSANA
ID NO 2:      SSSTQDYRIASEAEIKAHTFYTALSANA
ID NO 3:      SIDGGIRAATSQEINELTYYTTLSANS
ID NO 4:     SASDGGKVVAATTAQIQEFTKYAGIAATA
ID NO 5:        TAGHALAASTQ GISEDLYSRL VEMATISQAA
ID NO 6:        TAGHALAASTQ GISEDLYSRL VEMATISQAA
ID NO 7:           AVGVTTTDFSNFKFYIQHGAAA
ID NO 8:           TVTTQDLSNFRFYLQHADAA
ID NO 9:           DIPTTQLEDFKFWVQYAAAT
ID NO 10:          DVSTSELDQFEFWVQYAAAS
ID NO 11:          SVSTSTLDELQLFAQWSAAA
ID NO 12:          SVSTSTLDELQLFSQWSAAA
ID NO 13:          DVSSSLLNNLDLFAQYSAAA
ID NO 14:          EVSQDLFNQFNLFAQYSAAA
ID NO 15:          PQDAYTASHADLVKYATYAGLA

ID NO 1:     YCRTVIPG      GRWSCPHCGVAS   NLQITKTFST   LITDTNVLVAV
ID NO 2:     YCRTVIPG      GQWSCPHCDVAP   NLNITKTFTT   LITDTNVLVAV
ID NO 3:     YCRTVIPG      ATWDCIHCDATE   DLKIIKTWST   LIYDTNAMVAR
ID NO 4:     YCRSVVPG      NKWDCVQCQKWVP  DGKIITTFTS   LLSDTNGYVLR
ID NO 5:     YADLCNIPST                   IIKGEKIYNSQTDINGWILR
ID NO 6:     YADLCNIPST                   IIKGEKIYNSQTDINGWILR
ID NO 7:     YC   NSEAAA GSKITCSNNGCPTVQGNGATIVTSF  VGSKTGIGGYVAT
ID NO 8:     YC   NFNTAV GKPVHCSAGNCPDIEKDAAIVVGSV  VGTKTGIGAYVAT
ID NO 9:     YCPNNYVAKD GEKLNCSVGNCPDVEAAGSTVKLSFS  DDTITDTAGFVAV
ID NO 10:    YYEADYTAQV GDKLSCSKGNCPEVEATGATVSYDFS  DSTITDTAGYIAV
ID NO 11:    YCSNNID  SK DSNLTCTANACPSVEEASTTMLLEFDLTNDFGGTAGFLAA
ID NO 12:    YCSNNID  SD DSNVTCTADACPSVEEASTKMLLEFDLTNNFGGTAGFLAA
ID NO 13:    YCDENLN  ST GTKLTCSVGNCPLVEAASTQSLDEFNESSSYGNPAGYLAA
ID NO 14:    YCGKNNDAPA GTNITCTGNACPEVEKADATFLYSFE  DSGVGDVTGFLAL
ID NO 15:    YQTTDAWPAS               RTVPKDTTLISSFD   HTLKGSSGYIAF

ID NO 1:     GEKEKTIYVV FRGTSSIRNA IADIVFVPVN YPPV    NGA KVHKGFLDSY
ID NO 2:     GENEKTIYVV FRGTSSIRNA IADIVFVPVN YPPV    NGA KVHKGFLDSY
ID NO 3:     GDSEKTIYIV FRGSSSIRNW IADLTFVPVS YPPV    SGT KVHKGFLDSY
ID NO 4:     SDKQKTIYLV FRGTNSFRSA ITDIVFNFSD YKPV    KGA KVHAGFLSSY
ID NO 5:     DDSSKEIITV FRGTGSDTNL QLDTNYTLTP FDTLPQCNGC EVHGGYYIGW
ID NO 6:     DDSSKEIITV FRGTGSDTNL QLDTNYTLTP FDTLPQCNSC EVHGGYYIGW
ID NO 7:     DSARKEIVVS FRGSINIRNW LTNLDFG QE  DCSL   VSGC GVHSGFQRAW
ID NO 8:     DNARKEIVVS VRGSINVRNW ITNFNFG QK  TCDL   VAGC GVHTGFLDAW
ID NO 9:     DNTNKAIVVA FRGSYSIRNW VTDATFP QT  DPGL   CDGC KAELGFWTAW
ID NO 10:    DHTNSAVVLA FRGSYSVRNW VADATFV HT  NPGL   CDGC LAELGFWSSW
ID NO 11:    DNTNKRLVVA FRGSSTIENW IANLDFILED NDDL    CTGC KVHTGFWKAW
ID NO 12:    DNTNKRLVVA FRGSSTIKNW IADLDFILQD NDDL    CTGC KVHTGFWKAW
ID NO 13:    DETNKLLVLS FRGSADLANW VANLNFGLED ASDL    CSGC EVHSGFWKAW
ID NO 14:    DNTNKLIVLS FRGSRSIENW IGNLNFDLKE INDI    CSGC RGHDGFTSSW
ID NO 15:    NEPCKEIIVA YRGTDSLIDW LTNLNFDKTA WPAN    ISNS LVHEGFLNAY

ID NO 1:     NEVQDKLVAE VKAQLDRHPG YKIVVTGHSL GGATAVLSALDLYHHGHA
ID NO 2:     NEVQDKLVAE VKAQLDRHPG YKIVVTGHSL GGATAVLSALDLYHHGHD
```

Figure 1 (cont.)

```
ID NO  3:  GEVQNELVAT VLDQFKQYPS YKVAVTGHSL GGATALLCALDLYQREEGLS
ID NO  4:  EQVVNDYFPV VQEQLTAHPT YKVIVTGHSL GGAQALLAGMDLYQREPRLS
ID NO  5:  VSVQDQVESL VKQQVSQYPD YALTVTGHSL GASLAALTAAQL SATYD
ID NO  6:  ISVQDQVESL VQQQVSQFPD YALTVTGHSL GASLAALTAAQL SATYD
ID NO  7:  NEISSQATAA VASARKANPS FNVISTGHSL GGAVAVLAAANLRVGGT
ID NO  8:  EEVAANVKAA VSAAKTANPT FKFVVTGHSL GGAVATIAAAYLRKDGF
ID NO  9:  KVVRDRIIKT LDELKPEHSD YKIVVVGHSL GAAIASLAAADLRTKNY
ID NO 10:  KLVRDDIIKE LKEVVAQNPN YELVVVGHSL GAAVATLAATDLRGKGYP
ID NO 11:  ESAADELTSK IKSAMSTYSG YTLYFTGHSL GGALATLGATVLRNDGY
ID NO 12:  EAAADNLTSK IKSAMSTYSG YTLYFTGHSL GGALATLGATVLRNDGY
ID NO 13:  SEIADTITSK VESALSDHSD YSLVLTGHSY GAALAALAATALRNSGH
ID NO 14:  RSVADTLRQK VEDAVREHPD YRVVFTGHSL GGALATVAGADLRGNGY
ID NO 15:  LVSMQQVQEA VDSLLAKCPD ATISFTGHSL GGALACISMVDTAQRHRGI

ID NO  1:     NIEIYTQG QPRIGTPAFA NYVIGT       KIPYQRLVHERDIVPHL
ID NO  2:     NIEIYTQG QPRIGTPEFA NYVIGT       KIPYQRLVNERDIVPHL
ID NO  3:  SSNLFLYTQG QPRVGDPAFA NYVVST       GIPYRRTVNERDIVPHL
ID NO  4:  PKNLSIFTVG GPRVGNPTFA YYVEST       GIPFQRTVHKRDIVPHV
ID NO  5:     NIRLYTFG EPRSGNQAFA SYMNDAFQASSPDTTQYFRVTHANDGIPNL
ID NO  6:     NIRLYTFG EPRS NQAFA SYMNDAFQASSPDTTQYFRVTHANDGIPNL
ID NO  7:     PVDIYTYG SPRVGNAQLS AFVSNQ       AGGEYRVTHADDPVPRL
ID NO  8:     PFDLYTYG SPRVGNDFFA NFVTQQ       TGAEYRVTHGDDPVPRL
ID NO  9:     DAILYAYA APRVANKPLA EFITNQ       GNNYRFTHNDDPVPKL
ID NO 10:      SAKLYAYA SPRVGNAALA KYITAQ       GNNFRFTHTNDPVPKL
ID NO 11:     SVELYTYG CPRIGNYALA EHITSQ       GSGANFRVTHLNDIVPRV
ID NO 12:     SVELYTYG CPRVGNYALA EHITSQ       GSGANFPVTHLNDIVPRV
ID NO 13:     SVELYNYG QPRLGNEALA TYITDQ       NKGGNYRVTHTNDIVPKL
ID NO 14:     DIDVFSYG APRVGNRAFA EFLTVQ       TGGTLYRITHTNDIVPRL
ID NO 15:     KMQMFTYG QPRTGNQAFA EYVENL       GHPVFRVVYRHDIVPRM

ID NO  1:  PPGAFGFLHA GEEFWIMK         DSSLRVCPNGIETDNCSNSIV
ID NO  2:  PPGAFGFLHA GEEFWIMK         DSSLRVCPNGIETDNCSNSIV
ID NO  3:  PPAAFGFLHA GEEYWITD       NSPETVQVCTSDLETSDCSNSIV
ID NO  4:  PPQSFGFLHP GVESWIKS        GTSNVQICTSEIETKDCSNSIV
ID NO  5:  PPVEQGYAHG GVEYWSV      DPYSAQNTFVCTGDEVQCCE AQGGQG
ID NO  6:  PPADEGYAHG VVEYWSV      DPYSAQNTFVCTGDEVQCCE AQGGQG
ID NO  7:  PPLIFGYRHT TPEFWLSGGGGDKVDYTISDVKVCEGAANLG CNGGTL
ID NO  8:  PPIVFGYRHT SPEYWLNG GPLDKDYTVTEIKVCEGIANVM CNGGTI
ID NO  9:  PLLTMGYVHI SPEYYITA   PDNTTVTDNQVTVLDGYVNFK GNTGTS
ID NO 10:  PLLSMGYVHV SPEYWITS   PNNATVSTSDIKVIDGDVSFD GNTGTG
ID NO 11:  PPMDFGFSQP SPEYWITS   GNGASVTASDIEVIEGINSTA GNAGEA
ID NO 12:  PPMDFGFSQP SPEYWITS   GTGASVTASDIELIEGINSTA GNAGEA
ID NO 13:  PPTLLGYHHF SPEYYISS   ADEATVTTTDVTEVTGIDATG GNDGTD
ID NO 14:  PPREFGYSHS SPEYWIKS   GTLVPVTRNDIVKIEGIDATG GNNQPN
ID NO 15:  PPMDLGFQHH GQEVWYEG         DENIKFCKGEGENLTCELGVP

ID NO  1:  PFT    SVIDHLSYLDMNTGL CL
ID NO  2:  PFT    SVIDHLSYLDMNTGL CL
ID NO  3:  PFT    SVLDHLSYFGINTGL CT
ID NO  4:  PFT    SILDHLSYFDINEGS CL
ID NO  5:  VN     NAHTTYF GMTSGACTW
ID NO  6:  VN     NAHTTYF GMTSGHCTW
ID NO  7:  GL     DIAAHLHYF QATDA CNAGGFSWR R
ID NO  8:  GL     DILAHITYF QSMAT CAPIAIPWK R
ID NO  9:  GGLPDLLAFHSHVWYFIHADACKGPGLPLR
```

Figure 1 (cont.)

```
ID NO 10:    LPLLTDFEAHIWYF VQVDA GKGPGLPFK R
ID NO 11:    TV   SVLAHLWYF FAISE CLL
ID NO 12:    TV   DVLAHLWYF FAISE CLL
ID NO 13:    GT   SIDAHRWYF IYISE CS
ID NO 14:    IP   DIPAHLWYF GLIGT CL
ID NO 15:    FSEL NAKDHSEYP GMH
```

| ID NO: | Micro organism | SEQ ID NO.: |
|---|---|---|
| 1. | Absidia reflexa | 3 |
| 2. | Absidia corymbifera | 4 |
| 3. | Rhizmucor miehei | 5 |
| 4. | Rhizopus delemar (oryzea) | 6 |
| 5. | Aspergillus niger | 7 |
| 6. | Aspergillus tubingensis | 8 |
| 7. | Fusarium oxysporum | 9 |
| 8. | Fusarium heterosporum | 10 |
| 9. | Aspergillus oryzae | 11 |
| 10. | Penicilium camembertii | 12 |
| 11. | Aspergillus foetidus | 13 |
| 12 | Aspergillus niger | 14 |
| 13. | Aspergillus oryzea | 15 |
| 14. | Thermomyces lanuginosus | 2 |
| 15. | Landerina penisapora | 16 |

Figure 1. Alignment of lipase sequences.

Figure 1 (cont.)

POLYPEPTIDES HAVING LIPASE ACTIVITY AND POLYNUCLEOTIDES ENCODING SAME

CROSS-REFERENCE TO RELATED APPLICATIONS

This application is a continuation of U.S. application Ser. No. 12/161,083 filed on Aug. 14, 2008 which claims priority to 35 U.S.C. 371 national application of PCT/US2007/060825 filed Jan. 22, 2007, which claims priority or the benefit under 35 U.S.C. 119 of U.S. provisional application No. 60/761,106 filed Jan. 23, 2006, the contents of which are fully incorporated herein by reference.

FIELD OF THE INVENTION

The present invention relates to polypeptides having lipase activity and polynucleotides encoding same.

BACKGROUND OF THE INVENTION

Lipases are useful, e.g., as detergent enzymes to remove lipid or fatty stains from clothes and other textiles, as additives to dough for bread and other baked products. Thus, a lipase derived from *Thermomyces lanuginosus* (synonym *Humicola lanuginosa*, EP 258 068 and EP 305 216) is sold for detergent use under the tradename Lipolase® (product of Novo Nordisk A/S). WO 0060063 describes variants of the *T. lanuginosus* lipase with a particularly good first-wash performance in a detergent solution. WO 9704079, WO 9707202 and WO 0032758 also disclose variants of the *T. lanuginosus* lipase. WO 02062973 discloses *T. lanuginosus* lipase with a C-terminal extension with reduced tendency to form odor.

SUMMARY OF THE INVENTION

The present invention relates to isolated polypeptides having lipase activity selected from the group consisting of lipases having an Average Relative Performance (RP) of at least 0.8 and a Benefit-Risk (BR) of at least 1.1 at the test conditions given in the specification.

The present invention also relates to lipase variants with reduced potential for odor generation and to a method of preparing them. It particularly relates to variants of the *Thermomyces lanuginosus* lipase having a preference for long fatty acid chains while at the same time having a good relative performance.

In a further aspect the invention relates to an isolated polynucleotide comprising a nucleotide sequence which encodes the polypeptide, a nucleic acid construct comprising the polynucleotide, a recombinant expression vector comprising the nucleic acid construct and a recombinant host cell comprising the nucleic acid construct.

The present invention also relates to a method for producing the lipases of the invention.
Sequence Listing
SEQ ID NO: 1 shows the DNA sequence encoding lipase from *Thermomyces lanoginosus*.
SEQ ID NO: 2 shows the amino acid sequence of a lipase from *Thermomyces lanuginosus*.
SEQ ID NO: 3-SEQ ID NO: 16 show sequences for alignment in FIG. 1
SEQ ID NO: 17 and SEQ ID NO: 18 show sequences used for alignment example.

BRIEF DESCRIPTION OF THE DRAWINGS

FIG. 1 shows alignment of corresponding (or homologous) positions in the lipase sequences of *Absidia reflexa*, *Absidia corymbefera*, *Rhizmucor miehei*, *Rhizopus delemar*, *Aspergillus niger*, *Aspergillus tubigensis*, *Fusarium oxysporum*, *Fusarium heterosporum*, *Aspergillus oryzea*, *Penicilium camembertii*, *Aspergillus foetidus*, *Aspergillus niger*, *Thermomyces lanoginosus* (synonym: *Humicola lanuginose*) and *Landerina penisapora*.

DEFINITIONS

Lipase activity: The term "lipase activity" is defined herein as a carboxylic ester hydrolase activity which catalyzes the hydrolysis of triacylglycerol under the formation of diacylglycerol and a carboxylate. For purposes of the present invention, lipase activity is determined according to the procedure described in "Lipase activity" in "Materials and Methods". One unit of lipase activity is defined as the amount of enzyme capable of releasing 1.0 micro mole of butyric acid per minute at 30° C., pH 7.

The polypeptides of the present invention have at least 70%, such at least 75% or 80% or 85% or 90%, more preferably at least 95%, even more preferably 96% or 97%, most preferably 98% or 99%, and even most preferably at least 100% of the lipase activity measured as Relative Performance of the polypeptide consisting of the amino acid sequence shown as the mature polypeptide of SEQ ID NO:2, with the substitutions T231R+N233R.

Isolated polypeptide: The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation.

The polypeptides of the present invention are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form."

Identity: The relatedness between two amino acid sequences or between two nucleotide sequences is described by the parameter "identity".

For purposes of the present invention, the alignment of two amino acid sequences is determined by using the Needle program from the EMBOSS package (available on the Internet at emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

The degree of identity between an amino acid sequence of the present invention ("invention sequence"; e.g. amino acids 1 to 269 of SEQ ID NO:2) and a different amino acid sequence ("foreign sequence") is calculated as the number of exact matches in an alignment of the two sequences, divided by the length of the "invention sequence" or the length of the "foreign sequence", whichever is the shortest. The result is expressed in percent identity.

An exact match occurs when the "invention sequence" and the "foreign sequence" have identical amino acid residues in the same positions of the overlap (in the alignment example below this is represented by "|"). The length of a sequence is the number of amino acid residues in the sequence (e.g. the length of SEQ ID NO:2 is 269).

In the alignment example below, the overlap is the amino acid sequence "HTWGER-NL" of Sequence A; or the amino acid sequence "HGWGEDANL" of Sequence B. In the example a gap is indicated by a "-".
Alignment Example

```
Sequence A:   ACMSHTWGER-NL
                   | ||| ||
Sequence B:        HGWGEDANLAMNPS
```

Polypeptide Fragment: The term "polypeptide fragment" is defined herein as a polypeptide having one or more amino acids deleted from the amino and/or carboxyl terminus of SEQ ID NO: 2 or a homologous sequence thereof, wherein the fragment has lipase activity.

Subsequence: The term "subsequence" is defined herein as a nucleotide sequence having one or more nucleotides deleted from the 5' and/or 3' end of SEQ ID NO: 1 or a homologous sequence thereof, wherein the subsequence encodes a polypeptide fragment having lipase activity.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form. In particular, it is preferred that the polynucleotides disclosed herein are in "essentially pure form", i.e., that the polynucleotide preparation is essentially free of other polynucleotide material with which it is natively associated. Herein, the term "substantially pure polynucleotide" is synonymous with the terms "isolated polynucleotide" and "polynucleotide in isolated form." The polynucleotides may be of genomic, cDNA, RNA, semisynthetic, synthetic origin, or any combinations thereof.

cDNA: The term "cDNA" is defined herein as a DNA molecule which can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA which is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polynucleotide encoding a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG. The coding sequence may a DNA, cDNA, or recombinant nucleotide sequence.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the invention, and which is operably linked to additional nucleotides that provide for its expression.

Host cell: The term "host cell", as used herein, includes any cell type which is susceptible to transformation, transfection, transduction, and the like with a nucleic acid construct comprising a polynucleotide of the present invention.

Modification: The term "modification" means herein any chemical modification of the polypeptide consisting of the mature polypeptide of SEQ ID NO: 2 as well as genetic manipulation of the DNA encoding that polypeptide. The modification(s) can be substitution(s), deletion(s) and/or insertions(s) of the amino acid(s) as well as replacement(s) of amino acid side chain(s).

Artificial variant: When used herein, the term "artificial variant" means a polypeptide having lipase activity produced by an organism expressing a modified nucleotide sequence of SEQ ID NO: 1. The modified nucleotide sequence is obtained through human intervention by modification of the nucleotide sequence disclosed in SEQ ID NO: 1.

Relative performance (RP): The term relative performance reflects performance of the enzyme variant compared to a reference enzyme when measured as the brightness of the color of the textile samples washed with that specific enzyme variant.

Benefit-Risk factor (BR): The Benefit-Risk factor describes the wash performance compared to risk for odor when the substrate is removed.

Conventions for Designation of Variants:

In describing lipase variants according to the invention, the following nomenclature is used for ease of reference:

Original amino acid(s):position(s):substituted amino acid(s)

According to this nomenclature, for instance the substitution of glutamic acid for glycine in position 195 is shown as G195E. A deletion of glycine in the same position is shown as G195*, and insertion of an additional amino acid residue such as lysine is shown as G195GK.

Where a specific lipase contains a "deletion" in comparison with other lipases and an insertion is made in such a position this is indicated as *36D for insertion of an aspartic acid in position 36.

Multiple mutations are separated by pluses, i.e.: R170Y+ G195E, representing mutations in positions 170 and 195 substituting tyrosine and glutamic acid for arginine and glycine, respectively.

X231 indicates the amino acid in a parent polypeptide corresponding to position 231, when applying the described alignment procedure. X231R indicates that the amino acid is replaced with R. For SEQ ID NO:2 X is T, and T231R thus indicates a substitution of T in position 231 with R. Where the amino acid in a position (e.g. 231) may be substituted by another amino acid selected from a group of amino acids, e.g. the group consisting of R and P and Y, this will be indicated by X231R/P/Y.

In all cases, the accepted IUPAC single letter or triple letter amino acid abbreviation is employed.

DETAILED DESCRIPTION OF THE INVENTION

Polypeptides Having Lipase Activity

The present invention relates to isolated polypeptides having lipase activity selected from the group consisting of lipases having a RP of at least 0.8 and a BR of at least 1.1 at the test conditions given in the specification.

In a preferred embodiment the lipase has a RP of at least 0.9, such as 1.0 or 1.1. In an even more preferred embodiment the lipase has a RP of at least 1.2, such as 1.3 or even 1.4.

In another preferred embodiment the lipase has a BR of at least 1.2, such as 1.3 or even 1.4. In an even more preferred embodiment the lipase has a BR of at least 1.5, such as 1.6 or even 1.7.

In a further aspect the lipase of the present invention further has a relative LU/A280 less than 1, such as less than 0.95 at the test conditions given in the specification. In a preferred embodiment the relative LU/A280 is less than 0.90, such as less than 0.85 or even less than 0.80.

In a further aspect, the present invention relates to isolated polypeptides having an amino acid sequence which is comprised by or comprises SEQ ID NO:2, or an allelic variant thereof, and which further has BR of at least 1.1 and RP of at least 0.8. In another aspect, the present invention relates to isolated polypeptides having an amino acid sequence which is comprised by or comprises the mature part of SEQ ID NO:2, or an allelic variant thereof, and which further has BR of at least 1.1 and RP of at least 0.8

In a still further aspect, the present invention relates to isolated polypeptides having an amino acid sequence which has a degree of identity to the mature polypeptide of SEQ ID NO: 2 (i.e., the mature polypeptide) of at least 80%, such as at least 85% or 90%, or at least 95%, preferably at least 97%, most preferably at least 98%, and even most preferably at least 99%, which have lipase activity (hereinafter "homologous polypeptides"). In a preferred aspect, the homologous polypeptides have an amino acid sequence which differs by ten amino acids, by nine amino acids, by eight amino acids, by seven amino acids, by six amino acids, preferably by five amino acids, more preferably by four amino acids, even more preferably by three amino acids, most preferably by two amino acids, and even most preferably by one amino acid from the mature polypeptide of SEQ ID NO: 2.

In a further aspect, the present invention relates to isolated polypeptides having lipase activity which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with (i) nucleotides 644 to 732 of SEQ ID NO: 1, (ii) the cDNA sequence contained in nucleotides 644 to 732 of SEQ ID NO: 1, (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual*, 2d edition, Cold Spring Harbor, N.Y.). A subsequence of SEQ ID NO: 1 contains at least 100 contiguous nucleotides or preferably at least 200 contiguous nucleotides. Moreover, the subsequence may encode a polypeptide fragment which has lipase activity.

The nucleotide sequence of SEQ ID NO: 1 or a subsequence thereof, as well as the amino acid sequence of SEQ ID NO: 2 or a fragment thereof, may be used to design a nucleic acid probe to identify and clone DNA encoding polypeptides having lipase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, or more preferably at least 800 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other organisms may, therefore, be screened for DNA which hybridizes with the probes described above and which encodes a polypeptide having lipase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1 or a subsequence thereof, the carrier material is used in a Southern blot.

For purposes of the present invention, hybridization indicates that the nucleotide sequence hybridizes to a labeled nucleic acid probe corresponding to the nucleotide sequence shown in SEQ ID NO: 1, its complementary strand, or a subsequence thereof, under very low to very high stringency conditions. Molecules to which the nucleic acid probe hybridizes under these conditions can be detected using X-ray film.

In a still further aspect, the present invention relates to artificial variants comprising a conservative substitution, deletion, and/or insertion of one or more amino acids of SEQ ID NO: 2 or the mature polypeptide thereof, said variants having a BR of at least 1.1 and a RP of at least 0.8. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for biological activity (i.e., lipase activity) to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309:59-64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochem. 30:10832-10837; U.S. Pat. No. 5,223,409; WO 92/06204), and region-directed mutagenesis (Derbyshire et al., 1986, Gene 46:145; Ner et al., 1988, DNA 7:127).

Mutagenesis/shuffling methods can be combined with high-throughput, automated screening methods to detect activity of cloned, mutagenized polypeptides expressed by host cells. (Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of amino acids 1 to 291 of SEQ ID NO: 2 is 10, preferably 9, more preferably 8, more preferably 7, more preferably at most 6, more preferably at most 5, more preferably 4, even more preferably 3, most preferably 2, and even most preferably 1.

Identification of Regions and Substitutions

Substitutions covered by the present application may be identified as disclosed in this section.

The positions referred to in Region I through Region IV below are the positions of the amino acid residues in SEQ ID NO:2. To find the corresponding (or homologous) positions in a different lipase, the procedure described in "Homology and alignment" is used.

Substitutions in Region I

Region I consists of amino acid residues surrounding the N-terminal residue E1. In this region it is preferred to substitute an amino acid of the parent lipase with a more positive amino acid.

Amino acid residues corresponding to the following positions are comprised by Region I: 2 to 11 and 223-239. The following positions are of particular interest: 4, 8, 11, 223, 229, 231, 233, 234, 236.

In particular the following substitutions have been identified: X4V, X231R and X233R.

In a preferred embodiment the variant lipase has at least 80%, such as 85% or 90%, such as at least 95% or 98% or 99% identity to SEQ ID NO:2

Substitutions in Region II

Region II consists of amino acid residues in contact with substrate on one side of the acyl chain and one side of the alcohol part. In this region it is preferred to substitute an amino acid of the parent lipase with a more positive amino acid or with a less hydrophobic amino acid.

Amino acid residues corresponding to the following positions are comprised by Region II: 202 to 211 and 249 to 269. The following positions are of particular interest: 202, 210, 211, 253, 254, 255, 256.

In particular the following substitutions have been identified: X202G, X255Y/V and X256K/R.

In a preferred embodiment the variant lipase has at least 80%, such as 85% or 90%, such as at least 95% or 98% or 99% identity to SEQ ID NO:2

Substitutions in Region III

Region III consists of amino acid residues that forms a flexible structure and thus allowing the substrate to get into the active site. In this region it is preferred to substitute an amino acid of the parent lipase with a more positive amino acid or a less hydrophobic amino acid.

Amino acid residues corresponding to the following positions are comprised by Region III: 82 to 102. The following positions are of particular interest: 86, 87, 90, 91, 95, 96, 99.

In particular the following substitutions have been identified: X86V and X90A/R.

In a preferred embodiment the variant lipase has at least 80%, such as 85% or 90%, such as at least 95% or 98% or 99% identity to SEQ ID NO:2

Substitutions in Region IV

Region IV consists of amino acid residues that binds electrostatically to a surface. In this region it is preferred to substitute an amino acid of the parent lipase with a more positive amino acid.

Amino acid residues corresponding to the following positions are comprised by Region IV: 27 and 54 to 62. The following positions are of particular interest: 27, 56, 57, 58, 60.

In particular the following substitutions have been identified: X27R, X58N/AG/T/P and X60V/S/G/N/R/K/A/L.

In a preferred embodiment the variant lipase has at least 80%, such as 85% or 90%, such as at least 95% or 98% or 99% identity to SEQ ID NO:2

Amino Acids at Other Positions

The parent lipase may optionally comprise substitution of other amino acids, particularly less than 10 or less than 5 such substitutions. Examples are substitutions corresponding to one or more of the positions 24, 46, 74, 81, 83, 127, 131, 137, 147, 150, 203, 206, 211, 263, 264, 265, 267 and 269 of SEQ ID NO: 2. In a particular embodiment there is a substitution in at least one of the positions corresponding to position 81, 147, 150, 227 and 249. In a preferred embodiment the at least one substitution is selected from the group consisting of X81Q/E, X147MN, X150G, X227G and X249R/I/L.

Further substitutions may, e.g., be made according to principles known in the art, e.g. substitutions described in WO 92/05249, WO 94/25577, WO 95/22615, WO 97/04079 and WO 97/07202.

Homology and Alignment

For purposes of the present invention, the degree of homology may be suitably determined by means of computer programs known in the art, such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-45), using GAP with the following settings for polypeptide sequence comparison: GAP creation penalty of 3.0 and GAP extension penalty of 0.1.

In the present invention, corresponding (or homologous) positions in the lipase sequences of *Absidia reflexa, Absidia corymbefera, Rhizmucor miehei, Rhizopus delemar, Aspergillus niger, Aspergillus tubigensis, Fusarium oxysporum, Fusarium heterosporum, Aspergillus oryzea, Penicilium camembertii, Aspergillus foetidus, Aspergillus niger, Thermomyces lanoginosus* (synonym: *Humicola lanuginose*) and *Landerina penisapora* are defined by the alignment shown in FIG. 1.

To find the homologous positions in lipase sequences not shown in the alignment, the sequence of interest is aligned to the sequences shown in FIG. 1. The new sequence is aligned to the present alignment in FIG. 1 by using the GAP alignment to the most homologous sequence found by the GAP program. GAP is provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-45). The following settings are used for polypeptide se-quence comparison: GAP creation penalty of 3.0 and GAP extension penalty of 0.1.

Any suitable parent lipase may be used. In a preferred embodiment, the parent lipase has a homology of at least 50% with the *T. lanuginosus* lipase (SEQ ID NO: 2), particularly at least 55%, at least 60%, at least 75%, at least 85%, at least 90%, more than 95%, 96%, 97% or more than 98% or 99%. In a particular embodiment the parent lipase is identical to the *T. lanuginosus* lipase (SEQ ID NO:2).

Sources of Polypeptides Having Lipase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide of the present invention may be a bacterial polypeptide. For example, the polypeptide may be a gram positive bacterial polypeptide such as a *Bacillus* polypeptide, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis*, or *Bacillus thuringiensis* polypeptide; or a *Streptomyces* polypeptide, e.g., a *Streptomyces lividans* or *Streptomyces murinus* polypeptide; or a gram negative bacterial polypeptide, e.g., an *E. coli* or a *Pseudomonas* sp. polypeptide.

A polypeptide of the present invention may also be a fungal polypeptide, and more preferably a yeast polypeptide such as a *Candida, Kluyveromyces, Pichia, Saccharomyces, Schizosaccharomyces*, or *Yarrowia* polypeptide; or more preferably a filamentous fungal polypeptide such as an *Acre-* monium, *Aspergillus, Aureobasidium, Cryptococcus, Filobasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium,* or *Trichoderma* polypeptide.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having lipase activity.

In another preferred aspect, the polypeptide is an *Aspergillus aculeatus, Aspergillus awamori, Aspergillus fumigatus, Aspergillus foetidus, Aspergillus japonicus, Aspergillus nidulans, Aspergillus niger, Aspergillus oryzae, Aspergillus turbigensis, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Thermomyces lanoginosus* (synonym: *Humicola lanuginose*), *Mucor miehei, Myceliophthora thermophila, Neurospora crassa, Penicillium purpurogenum, Trichoderma harzianum, Trichoderma koningii, Trichoderma longibrachiatum, Trichoderma reesei,* or *Trichoderma viride* polypeptide.

In another preferred aspect, the polypeptide is a *Thermomyces* polypeptide.

In a more preferred aspect, the polypeptide is a *Thermomyces lanuginosus* polypeptide, e.g., the polypeptide of SEQ ID NO: 2 with mutations as disclosed in the present application.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of another microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention.

Techniques for producing fusion polypeptides are known in the art, and include ligating the coding sequences encoding the polypeptides so that they are in frame and that expression of the fused polypeptide is under control of the same promoter(s) and terminator.

Polynucleotides

The present invention also relates to isolated polynucleotides having a nucleotide sequence which encode a polypeptide of the present invention. The present invention also encompasses nucleotide sequences which encode a polypeptide being a variant of the amino acid sequence of SEQ ID NO: 2 or the mature polypeptide thereof, which differ from the encoding polynucleotide by virtue of the degeneracy of the genetic code. The present invention also relates to subsequences of SEQ ID NO: 1 which encode fragments of SEQ ID NO: 2 that have lipase activity, said fragments having a BR of at least 1.1 and a RP of at least 0.8.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: *A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Thermomyces*, or another or related organism and thus, for example, may be an allelic or species variant of the polypeptide encoding region of the nucleotide sequence.

The present invention also relates to polynucleotides having nucleotide sequences which have a degree of identity to the mature polypeptide coding sequence of SEQ ID NO: 1 of at least 60%, preferably at least 65%, more preferably at least 70%, more preferably at least 75%, more preferably at least 80%, more preferably at least 85%, more preferably at least 90%, even more preferably at least 95%, and most preferably at least 97%, 98%, or 99% identity, which encode an active polypeptide having lipase activity and BR of at least 1.1 and RP of at least 0.8.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermo stability, pH optimum, or the like. The variant sequence may be constructed on the basis of the nucleotide sequence presented as the polypeptide encoding region of SEQ ID NO: 1, e.g., a subsequence thereof, and/or by introduction of nucleotide substitutions which do not give rise to another amino acid sequence of the polypeptide encoded by the nucleotide sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for lipase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

The present invention also relates to isolated polynucleotides encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) of SEQ ID NO: 1, (ii) the cDNA sequence contained in SEQ ID NO: 1, or (iii) a complementary strand of (i) or (ii); or allelic variants and subsequences thereof (Sambrook et al., 1989, supra), as defined herein.

The present invention also relates to isolated polynucleotides obtained by (a) hybridizing a population of DNA under very low, low, medium, medium-high, high, or very high stringency conditions with (i) nucleotides SEQ ID NO: 1, (ii) the cDNA sequence contained in nucleotides of SEQ ID NO: 1, or (iii) a complementary strand of (i) or (ii); and (b) isolating the hybridizing polynucleotide, which encodes a polypeptide having lipase activity.

Nucleic Acid Constructs

The present invention also relates to nucleic acid constructs comprising an isolated polynucleotide of the present invention operably linked to one or more control sequences which direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionine (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described above may be joined together to produce a recombinant expression vector which may include one or more convenient restriction sites to allow for insertion or substitution of the nucleotide sequence encoding the polypeptide at such sites. Alternatively, a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

A conditionally essential gene may function as a non-antibiotic selectable marker. Non-limiting examples of bacterial conditionally essential non-antibiotic selectable markers are the dal genes from *Bacillus subtilis*, *Bacillus licheniformis*, or other Bacilli, that are only essential when the bacterium is cultivated in the absence of D-alanine. Also the genes encoding enzymes involved in the turnover of UDP-galactose can function as conditionally essential markers in a cell when the cell is grown in the presence of galactose or grown in a medium which gives rise to the presence of galactose. Non-limiting examples of such genes are those from *B. subtilis* or *B. licheniformis* encoding UTP-dependent phosphorylase (EC 2.7.7.10), UDP-glucose-dependent uridylyltransferase (EC 2.7.7.12), or UDP-galactose epimerase (EC 5.1.3.2). Also a xylose isomerase gene such as xylA, of Bacilli can be used as selectable markers in cells grown in minimal medium with xylose as sole carbon source. The genes necessary for utilizing gluconate, gntK, and gntP can also be used as selectable markers in cells grown in minimal medium with gluconate as sole carbon source. Other examples of conditionally essential genes are known in the art. Antibiotic selectable markers confer antibiotic resistance to such antibiotics as ampicillin, kanamycin, chloramphenicol, erythromycin, tetracycline, neomycin, hygromycin or methotrexate.

Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98:61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular microorganisms are bacterial cells such as gram positive bacteria including, but not limited to, a *Bacillus* cell, e.g., *Bacillus alkalophilus*, *Bacillus amyloliquefaciens*, *Bacillus brevis*, *Bacillus circulans*, *Bacillus clausii*, *Bacillus coagulans*, *Bacillus lautus*, *Bacillus lentus*, *Bacillus licheniformis*, *Bacillus megaterium*, *Bacillus stearothermophilus*, *Bacillus subtilis*, and *Bacillus thuringiensis*; or a *Streptomyces* cell, e.g., *Streptomyces lividans* and *Streptomyces murinus*, or gram negative bacteria such as *E. coli* and

*Pseudomonas* sp. In a preferred aspect, the bacterial host cell is a *Bacillus lentus*, *Bacillus licheniformis*, *Bacillus stearothermophilus*, or *Bacillus subtilis* cell. In another preferred aspect, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred aspect, the yeast host cell is a *Candida*, *Hansenula*, *Kluyveromyces*, *Pichia*, *Saccharomyces*, *Schizosaccharomyces*, or *Yarrowia* cell.

In a most preferred aspect, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium*, *Aspergillus*, *Aureobasidium*, *Bjerkandera*, *Ceriporiopsis*, *Coprinus*, *Coriolus*, *Cryptococcus*, *Filobasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

In a most preferred aspect, the filamentous fungal host cell is an *Aspergillus awamori*, *Aspergillus fumigatus*, *Aspergillus foetidus*, *Aspergillus japonicus*, *Aspergillus nidulans*, *Aspergillus niger* or *Aspergillus oryzae* cell. In another most preferred aspect, the filamentous fungal host cell is a *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, or *Fusarium venenatum* cell. In another most preferred aspect, the filamentous fungal host cell is a *Bjerkandera adusta*, *Ceriporiopsis aneirina*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, or *Ceriporiopsis subvermispora*, *Coprinus cinereus*, *Coriolus hirsutus*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* strain cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention, comprising (a) cultivating a cell, which in its wild-type form is capable of producing the polypeptide, under conditions conducive for production of the polypeptide; and (b) recovering the polypeptide. Preferably, the cell is of the genus *Aspergillus*, and more preferably *Aspergillus Oryzae*.

The present invention also relates to methods for producing a polypeptide of the present invention, comprising (a) cultivating a host cell under conditions conducive for production of the polypeptide; and (b) recovering the polypeptide.

The present invention also relates to methods for producing a polypeptide of the present invention, comprising (a) cultivating a host cell under conditions conducive for production of the polypeptide, wherein the host cell comprises a mutant nucleotide sequence having at least one mutation in the mature polypeptide coding region of SEQ ID NO: 1, wherein the mutant nucleotide sequence encodes a polypeptide which is a lipase comprised by or comprising the polypeptide of SEQ ID NO: 2, and (b) recovering the polypeptide. In a preferred embodiment the nucleotide sequence encodes a polypeptide which is a lipase comprised by or comprising the mature part of the polypeptide of SEQ ID NO: 2, and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Compositions

The present invention also relates to compositions comprising a polypeptide of the present invention. Preferably, the compositions are enriched in such a polypeptide. The term "enriched" indicates that the lipase activity of the composition has been increased, e.g., with an enrichment factor of 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, or *Aspergillus oryzae*; *Fusarium*, preferably *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sulphureum*, *Fusarium toruloseum*, *Fusarium trichothecioides*, or *Fusarium venenatum*; *Humicola*, preferably *Humicola insolens* or *Humicola lanuginosa*; or *Trichoderma*, preferably *Trichoderma harzianum*, *Trichoderma koningii*, *Trichoderma longibrachiatum*, *Trichoderma reesei*, or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Detergent Applications

The enzyme of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

Enzymes

In a specific aspect, the invention provides a detergent additive comprising the enzyme of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases:

Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 68, 76, 87, 97, 101, 104, 106, 120, 123, 167, 170, 194, 206, 218, 222, 224, 235, 245, 252 and 274, and amongst other variants with the following mutations: (K27R, V104Y, N123S, T124A), (N76D, S103A, V104I), or (S101G, S103A, V104I, G159D, A232V, Q236H, Q245R, N248D, N252K).

Preferred commercially available protease enzymes include ALCALASE™, SAVNASE™, PRIMASET™, DURALASE™, ESPERASE™, CORONASE™, POLARZYME™ and KANNASE™ (Novozymes A/S), MAXATASE™, MAXACAL™, MAXAPEM™, PROPERASE™, PURAFECT™, PURAFECT PRIME™, PURAFECT OXP™, FN2, FN3 and FN4 (Genencor International Inc.).

Lipases:

Lipases include those of bacterial or fungal origin. Chemically modified or protein engineered mutants are included. Examples of useful lipases include lipases from *Humicola* (synonym *Thermomyces*), e.g. from *H. lanuginosa* (synonymous *T. lanuginosus*) as described in EP 258 068 and EP 305 216 or from *H. insolens* as described in WO 96/13580, a *Pseudomonas* lipase, e.g. from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Other commercially available lipase enzymes include LIPOLASE™, LIPOLASE ULTRA™ and LIPEX™ (Novozymes A/S).

Preferred lipases are lipases of the present invention.

Amylases:

Suitable amylases (a and/or (3) include those of bacterial or fungal origin. Chemically modified or protein engineered mutants are included. Amylases include, for example, α-amylases obtained from *Bacillus*, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are DURAMYL™, TERMAMYL™, STAINZYME™, STAINZYME ULTRA™, FUNGAMYL™ and BAN™ (Novozymes A/S), RAPIDASE™ and PURASTAR™ (from Genencor International Inc.).

Cellulases:

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include RENOZYME™, CELLUZYME™, and CAREZYME™ (Novozymes A/S), CLAZINASE™, and PURADAX HA™ (Genencor International Inc.), and KAC-500(B)™ (Kao Corporation).

Peroxidases/Oxidases:

Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257.

Commercially available peroxidases include GUARDZYME™ (Novozymes A/S).

Detergents

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethylene glycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0% to 60% by weight.

When included therein the detergent will usually contain from about 0% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a H2O2 source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.001-100 mg of enzyme protein per liter of wash liquor, such as 0.01-50 mg or 0.03-30 mg, preferably 0.05-5 mg of enzyme protein per liter of wash liquor, in particular 0.1-1 mg of enzyme protein per liter of wash liquor.

The enzyme of the invention may additionally be incorporated in the detergent formulations disclosed in WO 97/07202, WO 04/041979, WO 04/074419, which is hereby incorporated as reference.

Uses

The present invention is also directed to methods for using the polypeptides having lipase activity.

The variants of the invention can be used in known applications of lipolytic enzymes by analogy with the prior art, e.g.:

A variant with lipase activity can be used in the pulp and paper industry, to remove pitch or to remove ink from used paper. WO 9213130, WO 9207138, JP 2160984 A, EP 374700.

A variant with phospholipase and/or galactolipase activity can be used in the preparation of dough, bread and cakes, e.g. to increase dough stability and dough handling properties, or to improve the elasticity of the bread or cake. WO 94/04035, WO 00/32758.

A variant with phospholipase activity can be used in a process for reducing the content of phospholipid in an edible oil. U.S. Pat. No. 5,264,367 (Metallgesellschaft, Röhm); K. Dahlke & H. Buchold, INFORM, 6 (12), 1284-91 (1995); H. Buchold, Fat Sci. Technol., 95 (8), 300-304 (1993); JP-A 2-153997 (Showa Sangyo); or EP 654,527 (Metallgesellschaft, Röhm).

A variant with lysophospholipase activity can be used to improve the filterability of an aqueous solution or slurry of carbohydrate origin, e.g. starch hydrolysate, especially a wheat starch hydrolysate. EP 219,269.

A variant with phospholipase activity can be used for the preparation of lyso-phospholipid, e.g. lyso-lecithin (EP 870840, JP-A 10-42884, JP-A 4-135456 or JP-A 2-49593) of for the production of mayonnaise (EP 628256, EP 398666 or EP 319064).

A variant with phospholipase activity may also be used in the processing of dairy and other food products, e.g. as described in EP 567,662 (Nestlé), EP 426,211 (Unilever), EP 166,284 (Nestlé), JP-A 57-189638 (Yakult) or U.S. Pat. No. 4,119,564 (Unile-ver).

A variant with phospholipase activity can be used in the leather industry. GB 2233665, EP 505920.

A variant with lipase activity may be used for removing fatty matter containing hydrophobic esters (e.g. triglycerides) during the finishing of textiles. WO 93/13256.

The present invention is further described by the following examples which should not be construed as limiting the scope of the invention.

EXAMPLES

Chemicals used as buffers and substrates were commercial products of at least reagent grade.

Media and Solutions

| Product | Tradename |
|---------|-----------|
| LAS: | Surfac PS |
| Zeolite A | Wessalith P |

Materials

| Product | Supplier |
|---------|----------|
| EMPA221 | EMPA St. Gallen, Lerchfeldstrasse 5, CH-9014 St. Gallen, Switzerland |

Example 1

Production of Enzyme

A plasmid containing the gene encoding the lipase is constructed and transformed into a suitable host cell using standard methods of the art.

Fermentation is carried out as a fed-batch fermentation using a constant medium temperature of 34° C. and a start volume of 1.2 liter. The initial pH of the medium is set to 6.5. Once the pH has increased to 7.0 this value is maintained through addition of 10% H3PO4. The level of dissolved oxygen in the medium is controlled by varying the agitation rate and using a fixed aeration rate of 1.0 liter air per liter medium per minute. The feed addition rate is maintained at a constant level during the entire fed-batch phase.

The batch medium contains maltose syrup as carbon source, urea and yeast extract as nitrogen source and a mixture of trace metals and salts. The feed added continuously during the fed-batch phase contains maltose syrup as carbon source whereas yeast extract and urea is added in order to assure a sufficient supply of nitrogen.

Purification of the lipase may be done by use of standard methods known in the art, e.g. by filtering the fermentation supernatant and subsequent hydrophobic chromatography and ion exchange chromatography, e.g. as described in EP 0 851 913 EP, Example 3.

Example 2

AMSA—Automated Mechanical Stress Assay—for Calculation of RP

The enzyme variants of the present application are tested using the Automatic Mechanical Stress Assay (AMSA). With the AMSA test the wash performance of a large quantity of small volume enzyme-detergent solutions can be examined. The AMSA plate has a number of slots for test solutions and a lid firmly squeezing the textile swatch to be washed against all the slot openings. During the washing time, the plate, test solutions, textile and lid are vigorously shaken to bring the test solution in contact with the textile and apply mechanical stress. For further description see WO 02/42740 especially the paragraph "Special method embodiments" at page 23-24. The containers, which contain the detergent test solution, consist of cylindrical holes (6 mm diam, 10 mm depth) in a metal plate. The stained fabric (test material) lies on the top of the metal plates and is used as a lid and seal on the containers. Another metal plate lies on the top of the stained fabric to avoid any spillage from each container. The two metal plate together with the stained fabric are vibrated up and down at a frequency of 30 Hz with an amplitude of 2 mm.

The assay is conducted under the experimental conditions specified below:

TABLE 1

| Test solution | 0.5 g/l LAS |
| | 0.52 g/l Na2CO3 |
| | 1.07 g/l Zeolite A |
| | 0.52 g/l Na3Citrate |
| Test solution volume | 160 micro l |
| pH | As is (≈9.9) |
| Wash time | 20 minutes |
| Temperature | 30° C. |
| Water hardness | 15° dH |
| | Ratio of $Ca^{2+}/Mg^{2+}/NaHCO_3$:4:1:7.5 |
| Enzyme concentration in test solution | 0.125, 0.25, 0.50, 1.0 mg ep/l |
| Drying | Wash performance: After washing the textile pieces is immediately flushed in tap water and air-dried at 85 C. in 5 min |
| | Odour: After washing the textile pieces is immediately flushed in tap water and dried at room temperature (20° C.) for 2 hours |
| Test material | Cream turmeric swatch as described below (EMPA221 used as cotton textile) |

Cream-turmeric swatches were prepared by mixing 5 g of turmeric (Santa Maria, Denmark) with 100 g cream (38% fat, Arla, Denmark) at 50° C., the mixture was left at this temperature for about 20 minutes and filtered (50° C.) to remove any un-dissolved particles. The mixture is cooled to 20° C. and woven cotton swatches, EMPA221, were immersed in the cream-turmeric mixture and afterwards allowed to dry at room temperature over night and frozen until use. The preparation of cream-tumeric swatches is disclosed in the patent WO 2006/125437.

The performance of the enzyme variant is measured as the brightness of the colour of the textile samples washed with that specific enzyme variant. Brightness can also be expressed as the intensity of the light reflected from the textile sample when luminated with white light. When the textile is stained the intensity of the reflected light is lower, than that of a clean textile. Therefore the intensity of the reflected light can be used to measure wash performance of an enzyme variant.

Color measurements are made with a professional flatbed scanner (PFU DL2400pro), which is used to capture an image of the washed textile samples. The scans are made with a resolution of 200 dpi and with an output color depth of 24 bits. In order to get accurate results, the scanner is frequently calibrated with a Kodak reflective IT8 target.

To extract a value for the light intensity from the scanned images, a special designed software application is used (Novozymes Color Vector Analyzer). The program retrieves the 24 bit pixel values from the image and converts them into values for red, green and blue (RGB). The intensity value (Int) is calculated by adding the RGB values together as vectors and then taking the length of the resulting vector:

$$\text{Int} = \sqrt{r^2 + g^2 + b^2}.$$

The wash performance (P) of the variants is calculated in accordance with the below formula:

$$P = \text{Int}(v) - \text{Int}(r)$$

where
Int(v) is the light intensity value of textile surface washed with enzyme, and
Int(r) is the light intensity value of textile surface washed without enzyme.

A relative performance score is given as the result of the AMSA wash in accordance with the definition:

Relative Performance scores (RP) are summing up the performances (P) of the tested enzyme variants against the reference enzyme:

$$RP = P(\text{test enzyme})/P(\text{reference enzyme}).$$

RPavg indicates the average relative performance compared to the reference enzyme at all three enzyme concentrations (0.125, 0.25, 0.5, 1.0 mg ep/l)

RPavg=avg(RP(0.125), RP(0.25) RP(0.5), RP(1.0))

A variant is considered to exhibit improved wash performance, if it performs better than the reference.
In the context of the present invention the reference enzyme is the mature part of SEQ ID NO:2 with the substitutions T231R+N233R.

Example 3

GC—Gas Chromatograph—for Calculation of Risk Factor

The butyric acid release from the lipase washed swatches were measured by Solid Phase Micro Extraction Gas Chromatography (SPME-GC) using the following method. Four textile pieces (5 mm in diameter), washed in the specified solution in Table 1 containing 1 mg/L lipase, were transferred to a Gas Chromatograph (GC) vial. The samples were analysed on a Varian 3800 GC equipped with a Stabilwax-DA w/Integra-Guard column (30 m, 0.32 mm ID and 0.25 micro-m df) and a Carboxen PDMS SPME fibre (75 micro-m). Each sample was preincubated for 10 min at 40° C. followed by 20 min sampling with the SPME fibre in the head-space over the textile pieces. The sample was subsequently injected onto the column (injector temperature=250° C.). Column flow=2 ml Helium/min. Column oven temperature gradient: 0 min=40° C., 2 min=40° C., 22 min=240° C., 32 min=240° C. The butyric acid was detected by FID detection and the amount of butyric acid was calculated based on a butyric acid standard curve.

The Risk Performance Odour, R, of a lipase variant is the ratio between the amount of released butyric acid from the lipase variant washed swatch and the amount of released butyric acid from a swatch washed with the mature part of the lipase of SEQ ID NO: 2, after both values have been corrected for the amount of released butyric acid from a non-lipase washed swatch. The risk (R) of the variants is calculated in accordance with the below formula:

Odour=measured in micro g buturic acid developed at 1 mg enzyme protein/l corrected for blank $Alpha_{test\ enzyme} = Odour_{test\ enzyme} - Blank$
$Alpha_{reference\ enzyme} = Odour_{reference\ enzyme} - Blank$
$R = Alpha_{test\ enzyme} / Alpha_{reference\ enzyme}$ A variant is considered to exhibit reduced odor compared to the reference, if the R factor is lower than 1.

Example 4

Activity (LU) Relative to Absorbance at 280 nm

The activity of a lipase relative to the absorbance at 280 nm is determined by the following assay:
LU/A280:
A substrate for lipase is prepared by emulsifying tributyrin (glycerin tributyrate) using gum Arabic as emulsifier. The hydrolysis of tributyrin at 30° C. at pH 7 or 9 is followed in a pH-stat titration experiment. One unit of lipase activity (1 LU) equals the amount of enzyme capable of releasing 1 micro mol butyric acid/min at pH 7.

The absorbance of the purified lipase at 280 nm is measured (A280) and the ratio LU/A280 is calculated. The relative LU/A280 is calculated as the LU/A280 of the variant divided by the LU/A280 of a reference enzyme. In the context of the present invention the reference enzyme is the mature part of SEQ ID NO:2 with the mutations T231R and N233R.

Example 5

BR—Benefit Risk

The Benefit Risk factor describing the performance compared to the reduced risk for odour smell is thus defined as:

$BR = RP_{avg}/R$

A variant is considered to exhibit improved wash performance and reduced odor, if the BR factor is higher than 1.

Applying the above methods the following results were obtained:

TABLE 2

| Variant | Mutations in mature part of polypeptide of SEQ ID NO: 2 | RP | BR | LU/A280 |
|---|---|---|---|---|
| 1 | I202G + T231R + N233R | 0.84 | 1.41 | not determined |
| 2 | I86V + L227G + T231R + N233R + P256K | 1.08 | 1.52 | 1700 |
| 3 | Q4V + S58N + V60S + T231R + N233R | 0.87 | 1.73 | 1950 |
| 4 | S58N + V60S + I90R + T231R, N233R | 1.06 | 1.27 | 2250 |
| 5 | I255Y + T231R + N233R | 1.19 | 1.17 | 3600 |
| 6 | I90A + T231R + N233R + I255V | 1.13 | 1.14 | 2700 |
| Reference | T231R + N233R | 1.00 | 1.00 | 3650 |
| 7 | G91A + E99K + T231R + N233R + Q249R + 270H + 271T + 272P + 273S + 274S + 275G + 276R + 277G + 278G + 279H + 280R | 0.43 | not determined | 850 |
| 8 | G91A + E99K + T231R, N233R + Q249R + 270H + 271T + 272P + 273S + 274S + 275G + 276R + 277G + 278G | 0.13 | not determined | 500 |

The reference lipase and variants 7 and 8 in Table 2 are described in WO 2000/060063.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

The invention claimed is:

1. An isolated variant of a parent lipase, wherein
the parent lipase comprises the amino acid sequence of the positions 1 to 269 of the mature polypeptide shown in SEQ ID NO: 2 or an amino acid sequence having at least 90% amino acid sequence identity with the amino acid sequence of the positions 1 to 269 of the mature polypeptide shown in SEQ ID NO: 2 and having a lipase activity, and
the variant lipase comprises one of the following modifications:
(1) I202G+T231R+N233R;
(2) I86V+L227G+T231R+N233R+P256K;
(3) Q4V+S58N+V60S+T231R+N233R;
(4) S58N+V60S+I90R+T231R+N233R;
(5) I255Y+T231R+N233R; and
(6) I90A+T231R+N233R+I255V;
and wherein the variant lipase has lipase activity, and further has an Average Relative Performance (RPave) of at least 0.8 and a Benefit Risk (BR) of at least 1.1 in comparison with those of the Reference lipase consisting of the amino acid sequence of the positions 1 to 269 of the mature polypeptide shown in SEQ ID NO: 2 which contains the modification T231R+N233R.

2. The variant lipase of claim 1, further comprising a substitution at one or more of positions 4, 8, 11, 223, 229, 234, 236 corresponding to the mature polypeptide SEQ ID NO: 2.

3. The variant lipase of claim 1, further comprising the substitution X4V corresponding to the mature polypeptide of SEQ ID NO: 2.

4. The variant lipase of claim 1, further comprising a substitution at one or more of positions 202 to 211 and 249 to 269 corresponding to the mature polypeptide of SEQ ID NO: 2.

5. The variant lipase of claim 1, further comprising a substitution at one or more of positions 202, 210, 211, 253, 254, 255, 256 corresponding to the mature polypeptide of SEQ ID NO: 2.

6. The variant lipase of claim 1, further comprising one or more of the substitutions: X202G, X255Y/V and X256K/R corresponding to the mature polypeptide of SEQ ID NO: 2.

7. The variant lipase of claim 1, further comprising a substitution at one more of positions 82 to 102 corresponding to the mature polypeptide of SEQ ID NO: 2.

8. The variant lipase of claim 1, further comprising a substitution at one or more of positions 86, 87, 90, 91, 95, 96, 99 corresponding to the mature polypeptide of SEQ ID NO: 2.

9. The variant lipase of claim 1, further comprising one or more of the substitutions: X86V and X90A/R corresponding to the mature polypeptide of SEQ ID NO: 2.

10. The variant lipase of claim 1, further comprising a substitution at one or more of positions 27 and 54 to 62 corresponding to the mature polypeptide of SEQ ID NO: 2.

11. The variant lipase of claim 1, further comprising a substitution at one or more of positions 27, 56, 57, 58, 60 corresponding to the mature polypeptide of SEQ ID NO: 2.

12. The variant lipase of claim 1, further comprising one or more of the substitutions: 27R, X58N/AG/T/P and X60V/S/G/N/R/K/A/L corresponding to the mature polypeptide of SEQ ID NO: 2.

13. The variant lipase of claim 1, wherein the parent lipase comprises an amino acid sequence having at least 95% amino acid sequence identity with the amino acid sequence of the positions 1 to 269 of the mature polypeptide shown in SEQ ID NO: 2.

14. The variant lipase of claim 1, wherein the parent lipase comprises an amino acid sequence having at least 97% amino acid sequence identity with the amino acid sequence of the positions 1 to 269 of the mature polypeptide shown in SEQ ID NO: 2.

15. The variant lipase of claim 1, wherein the parent lipase comprises an amino acid sequence having at least 98% amino acid sequence identity with the amino acid sequence of the positions 1 to 269 of the mature polypeptide shown in SEQ ID NO: 2.

16. The variant lipase of claim 1, wherein the parent lipase comprises an amino acid sequence having at least 99% amino acid sequence identity with the amino acid sequence of the positions 1 to 269 of the mature polypeptide shown in SEQ ID NO: 2.

17. The variant lipase of claim 1, wherein the parent lipase comprises the amino acid sequence of the positions 1 to 269 of the mature polypeptide shown in SEQ ID NO: 2.

18. A polynucleotide comprising a nucleotide sequence encoding the variant lipase of claim 1.

19. A nucleic acid construct comprising the polynucleotide of claim 18 operably linked to one or more control sequences that directs the production of the variant lipase in an expression host.

20. A recombinant expression vector comprising the nucleic acid construct of claim 19.

21. An isolated recombinant host cell comprising the nucleic acid construct of claim 19.

22. A method for producing a variant lipase, comprising:
(a) culturing the recombinant host cell according to claim 21; and
(b) recovering the variant lipase.

23. A detergent composition comprising the variant lipase of claim 1.

24. A washing composition comprising the variant lipase of claim 1.

25. The washing composition of claim 24, for removing pitch in the pulp or paper industry, or removing ink from used paper.

26. A dough composition comprising the variant lipase of claim 1.

* * * * *

SEQUENCE LISTING

<160> NUMBER OF SEQ ID NOS: 18

<210> SEQ ID NO 1
<211> LENGTH: 873
<212> TYPE: DNA
<213> ORGANISM: Thermomyces lanuginosus
<220> FEATURE:
<221> NAME/KEY: CDS
<222> LOCATION: (1)..(873)
<220> FEATURE:
<221> NAME/KEY: sig_peptide
<222> LOCATION: (1)..(51)
<220> FEATURE:
<221> NAME/KEY: propep
<222> LOCATION: (52)..(66)
<220> FEATURE:
<221> NAME/KEY: mat_peptide
<222> LOCATION: (67)..()

<400> SEQUENCE: 1

```
atg agg agc tcc ctt gtg ctg ttc ttt gtc tct gcg tgg acg gcc ttg      48
Met Arg Ser Ser Leu Val Leu Phe Phe Val Ser Ala Trp Thr Ala Leu
        -20             -15                 -10 gcc agt cct att cgt cga gag gtc tcg cag gat ctg ttt aac cag ttc      96
Ala Ser Pro Ile Arg Arg Glu Val Ser Gln Asp Leu Phe Asn Gln Phe
 -5              -1  1              5                   10 aat ctc ttt gca cag tat tct gca gcc gca tac tgc gga aaa aac aat     144
Asn Leu Phe Ala Gln Tyr Ser Ala Ala Ala Tyr Cys Gly Lys Asn Asn
                 15                  20                  25 gat gcc cca gct ggt aca aac att acg tgc acg gga aat gcc tgc ccc     192
Asp Ala Pro Ala Gly Thr Asn Ile Thr Cys Thr Gly Asn Ala Cys Pro
                 30                  35                  40 gag gta gag aag gcg gat gca acg ttt ctc tac tcg ttt gaa gac tct     240
Glu Val Glu Lys Ala Asp Ala Thr Phe Leu Tyr Ser Phe Glu Asp Ser
             45                  50                  55 gga gtg ggc gat gtc acc ggc ttc ctt gct ctc gac aac acg aac aaa     288
Gly Val Gly Asp Val Thr Gly Phe Leu Ala Leu Asp Asn Thr Asn Lys
         60                  65                  70 ttg atc gtc ctc tct ttc cgt ggc tct cgt tcc ata gag aac tgg atc     336
Leu Ile Val Leu Ser Phe Arg Gly Ser Arg Ser Ile Glu Asn Trp Ile
 75                  80                  85                  90 ggg aat ctt aac ttc gac ttg aaa gaa ata aat gac att tgc tcc ggc     384
Gly Asn Leu Asn Phe Asp Leu Lys Glu Ile Asn Asp Ile Cys Ser Gly
                 95                 100                 105 tgc agg gga cat gac ggc ttc act tcg tcc tgg agg tct gta gcc gat     432
Cys Arg Gly His Asp Gly Phe Thr Ser Ser Trp Arg Ser Val Ala Asp
                110                 115                 120 acg tta agg cag aag gtg gag gat gct gtg agg gag cat ccc gac tat     480
Thr Leu Arg Gln Lys Val Glu Asp Ala Val Arg Glu His Pro Asp Tyr
            125                 130                 135 cgc gtg gtg ttt acc gga cat agc ttg ggt ggt gca ttg gca act gtt     528
Arg Val Val Phe Thr Gly His Ser Leu Gly Gly Ala Leu Ala Thr Val
        140                 145                 150 gcc gga gca gac ctg cgt gga aat ggg tat gat atc gac gtg ttt tca     576
Ala Gly Ala Asp Leu Arg Gly Asn Gly Tyr Asp Ile Asp Val Phe Ser
155                 160                 165                 170 tat ggc gcc ccc cga gtc gga aac agg gct ttt gca gaa ttc ctg acc     624
Tyr Gly Ala Pro Arg Val Gly Asn Arg Ala Phe Ala Glu Phe Leu Thr
                175                 180                 185 gta cag acc ggc gga aca ctc tac cgc att acc cac acc aat gat att     672
Val Gln Thr Gly Gly Thr Leu Tyr Arg Ile Thr His Thr Asn Asp Ile
            190                 195                 200
```

```
gtc cct aga ctc ccg ccg cgc gaa ttc ggt tac agc cat tct agc cca    720
Val Pro Arg Leu Pro Pro Arg Glu Phe Gly Tyr Ser His Ser Ser Pro
    205                 210                 215 gag tac tgg atc aaa tct gga acc ctt gtc ccc gtc acc cga aac gat    768
Glu Tyr Trp Ile Lys Ser Gly Thr Leu Val Pro Val Thr Arg Asn Asp
    220                 225                 230 atc gtg aag ata gaa ggc atc gat gcc acc ggc ggt aat aac cag cct    816
Ile Val Lys Ile Glu Gly Ile Asp Ala Thr Gly Gly Asn Asn Gln Pro
235                 240                 245                 250 aac att ccg gat atc cct gcg cac cta tgg tac ttc ggg tta att ggg    864
Asn Ile Pro Asp Ile Pro Ala His Leu Trp Tyr Phe Gly Leu Ile Gly
                255                 260                 265 aca tgt ctt                                                        873
Thr Cys Leu <210> SEQ ID NO 2
<211> LENGTH: 291
<212> TYPE: PRT
<213> ORGANISM: Thermomyces lanuginosus

<400> SEQUENCE: 2

Met Arg Ser Ser Leu Val Leu Phe Phe Val Ser Ala Trp Thr Ala Leu
        -20                 -15                 -10

Ala Ser Pro Ile Arg Arg Glu Val Ser Gln Asp Leu Phe Asn Gln Phe
    -5                  -1  1               5                  10

Asn Leu Phe Ala Gln Tyr Ser Ala Ala Tyr Cys Gly Lys Asn Asn
                15                  20                  25

Asp Ala Pro Ala Gly Thr Asn Ile Thr Cys Thr Gly Asn Ala Cys Pro
            30                  35                  40

Glu Val Glu Lys Ala Asp Ala Thr Phe Leu Tyr Ser Phe Glu Asp Ser
        45                  50                  55

Gly Val Gly Asp Val Thr Gly Phe Leu Ala Leu Asp Asn Thr Asn Lys
    60                  65                  70

Leu Ile Val Leu Ser Phe Arg Gly Ser Arg Ser Ile Glu Asn Trp Ile
75                  80                  85                  90

Gly Asn Leu Asn Phe Asp Leu Lys Glu Ile Asn Asp Ile Cys Ser Gly
                95                  100                 105

Cys Arg Gly His Asp Gly Phe Thr Ser Ser Trp Arg Ser Val Ala Asp
            110                 115                 120

Thr Leu Arg Gln Lys Val Glu Asp Ala Val Arg Glu His Pro Asp Tyr
        125                 130                 135

Arg Val Val Phe Thr Gly His Ser Leu Gly Gly Ala Leu Ala Thr Val
    140                 145                 150

Ala Gly Ala Asp Leu Arg Gly Asn Gly Tyr Asp Ile Asp Val Phe Ser
155                 160                 165                 170

Tyr Gly Ala Pro Arg Val Gly Asn Arg Ala Phe Ala Glu Phe Leu Thr
                175                 180                 185

Val Gln Thr Gly Gly Thr Leu Tyr Arg Ile Thr His Thr Asn Asp Ile
            190                 195                 200

Val Pro Arg Leu Pro Pro Arg Glu Phe Gly Tyr Ser His Ser Ser Pro
        205                 210                 215

Glu Tyr Trp Ile Lys Ser Gly Thr Leu Val Pro Val Thr Arg Asn Asp
    220                 225                 230

Ile Val Lys Ile Glu Gly Ile Asp Ala Thr Gly Gly Asn Asn Gln Pro
235                 240                 245                 250

Asn Ile Pro Asp Ile Pro Ala His Leu Trp Tyr Phe Gly Leu Ile Gly
                255                 260                 265
```

Thr Cys Leu

<210> SEQ ID NO 3
<211> LENGTH: 265
<212> TYPE: PRT
<213> ORGANISM: Absidia reflexa

<400> SEQUENCE: 3

```
Ser Ser Ser Ser Thr Gln Asp Tyr Arg Ile Ala Ser Glu Ala Glu Ile
1               5                   10                  15

Lys Ala His Thr Phe Tyr Thr Ala Leu Ser Ala Asn Ala Tyr Cys Arg
            20                  25                  30

Thr Val Ile Pro Gly Gly Arg Trp Ser Cys Pro His Cys Gly Val Ala
        35                  40                  45

Ser Asn Leu Gln Ile Thr Lys Thr Phe Ser Thr Leu Ile Thr Asp Thr
    50                  55                  60

Asn Val Leu Val Ala Val Gly Glu Lys Glu Lys Thr Ile Tyr Val Val
65                  70                  75                  80

Phe Arg Gly Thr Ser Ser Ile Arg Asn Ala Ile Ala Asp Ile Val Phe
                85                  90                  95

Val Pro Val Asn Tyr Pro Pro Val Asn Gly Ala Lys Val His Lys Gly
            100                 105                 110

Phe Leu Asp Ser Tyr Asn Glu Val Gln Asp Lys Leu Val Ala Glu Val
        115                 120                 125

Lys Ala Gln Leu Asp Arg His Pro Gly Tyr Lys Ile Val Val Thr Gly
    130                 135                 140

His Ser Leu Gly Gly Ala Thr Ala Val Leu Ser Ala Leu Asp Leu Tyr
145                 150                 155                 160

His His Gly His Ala Asn Ile Glu Ile Tyr Thr Gln Gly Gln Pro Arg
                165                 170                 175

Ile Gly Thr Pro Ala Phe Ala Asn Tyr Val Ile Gly Thr Lys Ile Pro
            180                 185                 190

Tyr Gln Arg Leu Val His Glu Arg Asp Ile Val Pro His Leu Pro Pro
        195                 200                 205

Gly Ala Phe Gly Phe Leu His Ala Gly Glu Glu Phe Trp Ile Met Lys
    210                 215                 220

Asp Ser Ser Leu Arg Val Cys Pro Asn Gly Ile Glu Thr Asp Asn Cys
225                 230                 235                 240

Ser Asn Ser Ile Val Pro Phe Thr Ser Val Ile Asp His Leu Ser Tyr
                245                 250                 255

Leu Asp Met Asn Thr Gly Leu Cys Leu
            260                 265
```

<210> SEQ ID NO 4
<211> LENGTH: 264
<212> TYPE: PRT
<213> ORGANISM: Absidia corymbifera

<400> SEQUENCE: 4

```
Ser Ser Ser Thr Gln Asp Tyr Arg Ile Ala Ser Glu Ala Glu Ile Lys
1               5                   10                  15

Ala His Thr Phe Tyr Thr Ala Leu Ser Ala Asn Ala Tyr Cys Arg Thr
            20                  25                  30

Val Ile Pro Gly Gly Gln Trp Ser Cys Pro His Cys Asp Val Ala Pro
        35                  40                  45
```

-continued

Asn Leu Asn Ile Thr Lys Thr Phe Thr Thr Leu Ile Thr Asp Thr Asn
    50                  55                  60

Val Leu Val Ala Val Gly Glu Asn Glu Lys Thr Ile Tyr Val Val Phe
65                  70                  75                  80

Arg Gly Thr Ser Ser Ile Arg Asn Ala Ile Ala Asp Ile Val Phe Val
                85                  90                  95

Pro Val Asn Tyr Pro Pro Val Asn Gly Ala Lys Val His Lys Gly Phe
            100                 105                 110

Leu Asp Ser Tyr Asn Glu Val Gln Asp Lys Leu Val Ala Glu Val Lys
            115                 120                 125

Ala Gln Leu Asp Arg His Pro Gly Tyr Lys Ile Val Thr Gly His
    130                 135                 140

Ser Leu Gly Gly Ala Thr Ala Val Leu Ser Ala Leu Asp Leu Tyr His
145                 150                 155                 160

His Gly His Asp Asn Ile Glu Ile Tyr Thr Gln Gly Gln Pro Arg Ile
                165                 170                 175

Gly Thr Pro Glu Phe Ala Asn Tyr Val Ile Gly Thr Lys Ile Pro Tyr
            180                 185                 190

Gln Arg Leu Val Asn Glu Arg Asp Ile Val Pro His Leu Pro Pro Gly
    195                 200                 205

Ala Phe Gly Phe Leu His Ala Gly Glu Glu Phe Trp Ile Met Lys Asp
    210                 215                 220

Ser Ser Leu Arg Val Cys Pro Asn Gly Ile Glu Thr Asp Asn Cys Ser
225                 230                 235                 240

Asn Ser Ile Val Pro Phe Thr Ser Val Ile Asp His Leu Ser Tyr Leu
                245                 250                 255

Asp Met Asn Thr Gly Leu Cys Leu
            260

<210> SEQ ID NO 5
<211> LENGTH: 269
<212> TYPE: PRT
<213> ORGANISM: Rhizomucor miehei

<400> SEQUENCE: 5

Ser Ile Asp Gly Gly Ile Arg Ala Ala Thr Ser Gln Glu Ile Asn Glu
1               5                   10                  15

Leu Thr Tyr Tyr Thr Thr Leu Ser Ala Asn Ser Tyr Cys Arg Thr Val
                20                  25                  30

Ile Pro Gly Ala Thr Trp Asp Cys Ile His Cys Asp Ala Thr Glu Asp
            35                  40                  45

Leu Lys Ile Ile Lys Thr Trp Ser Thr Leu Ile Tyr Asp Thr Asn Ala
    50                  55                  60

Met Val Ala Arg Gly Asp Ser Glu Lys Thr Ile Tyr Ile Val Phe Arg
65                  70                  75                  80

Gly Ser Ser Ser Ile Arg Asn Trp Ile Ala Asp Leu Thr Phe Val Pro
                85                  90                  95

Val Ser Tyr Pro Pro Val Ser Gly Thr Lys Val His Lys Gly Phe Leu
            100                 105                 110

Asp Ser Tyr Gly Glu Val Gln Asn Glu Leu Val Ala Thr Val Leu Asp
            115                 120                 125

Gln Phe Lys Gln Tyr Pro Ser Tyr Lys Val Ala Val Thr Gly His Ser
    130                 135                 140

Leu Gly Gly Ala Thr Ala Leu Leu Cys Ala Leu Asp Leu Tyr Gln Arg
145                 150                 155                 160

```
Glu Glu Gly Leu Ser Ser Ser Asn Leu Phe Leu Tyr Thr Gln Gly Gln
                165                 170                 175

Pro Arg Val Gly Asp Pro Ala Phe Ala Asn Tyr Val Val Ser Thr Gly
            180                 185                 190

Ile Pro Tyr Arg Arg Thr Val Asn Glu Arg Asp Ile Val Pro His Leu
        195                 200                 205

Pro Pro Ala Ala Phe Gly Phe Leu His Ala Gly Glu Glu Tyr Trp Ile
    210                 215                 220

Thr Asp Asn Ser Pro Glu Thr Val Gln Val Cys Thr Ser Asp Leu Glu
225                 230                 235                 240

Thr Ser Asp Cys Ser Asn Ser Ile Val Pro Phe Thr Ser Val Leu Asp
                245                 250                 255

His Leu Ser Tyr Phe Gly Ile Asn Thr Gly Leu Cys Thr
                260                 265

<210> SEQ ID NO 6
<211> LENGTH: 271
<212> TYPE: PRT
<213> ORGANISM: Rhizopus oryzae

<400> SEQUENCE: 6

Ser Ala Ser Asp Gly Gly Lys Val Val Ala Thr Thr Ala Gln Ile
1               5                   10                  15

Gln Glu Phe Thr Lys Tyr Ala Gly Ile Ala Ala Thr Ala Tyr Cys Arg
                20                  25                  30

Ser Val Val Pro Gly Asn Lys Trp Asp Cys Val Gln Cys Gln Lys Trp
            35                  40                  45

Val Pro Asp Gly Lys Ile Ile Thr Thr Phe Thr Ser Leu Leu Ser Asp
50                  55                  60

Thr Asn Gly Tyr Val Leu Arg Ser Asp Lys Gln Lys Thr Ile Tyr Leu
65                  70                  75                  80

Val Phe Arg Gly Thr Asn Ser Phe Arg Ser Ala Ile Thr Asp Ile Val
                85                  90                  95

Phe Asn Phe Ser Asp Tyr Lys Pro Val Lys Gly Ala Lys Val His Ala
            100                 105                 110

Gly Phe Leu Ser Ser Tyr Glu Gln Val Val Asn Asp Tyr Phe Pro Val
        115                 120                 125

Val Gln Glu Gln Leu Thr Ala His Pro Thr Tyr Lys Val Ile Val Thr
    130                 135                 140

Gly His Ser Leu Gly Gly Ala Gln Ala Leu Leu Ala Gly Met Asp Leu
145                 150                 155                 160

Tyr Gln Arg Glu Pro Arg Leu Ser Pro Lys Asn Leu Ser Ile Phe Thr
                165                 170                 175

Val Gly Gly Pro Arg Val Gly Asn Pro Thr Phe Ala Tyr Tyr Val Glu
            180                 185                 190

Ser Thr Gly Ile Pro Phe Gln Arg Thr Val His Lys Arg Asp Ile Val
        195                 200                 205

Pro His Val Pro Pro Gln Ser Phe Gly Phe Leu His Pro Gly Val Glu
    210                 215                 220

Ser Trp Ile Lys Ser Gly Thr Ser Asn Val Gln Ile Cys Thr Ser Glu
225                 230                 235                 240

Ile Glu Thr Lys Asp Cys Ser Asn Ser Ile Val Pro Phe Thr Ser Ile
                245                 250                 255

Leu Asp His Leu Ser Tyr Phe Asp Ile Asn Glu Gly Ser Cys Leu
            260                 265                 270
```

<210> SEQ ID NO 7
<211> LENGTH: 267
<212> TYPE: PRT
<213> ORGANISM: Aspergillus niger

<400> SEQUENCE: 7

Thr Ala Gly His Ala Leu Ala Ala Ser Thr Gln Gly Ile Ser Glu Asp
1               5                   10                  15

Leu Tyr Ser Arg Leu Val Glu Met Ala Thr Ile Ser Gln Ala Ala Tyr
            20                  25                  30

Ala Asp Leu Cys Asn Ile Pro Ser Thr Ile Ile Lys Gly Glu Lys Ile
        35                  40                  45

Tyr Asn Ser Gln Thr Asp Ile Asn Gly Trp Ile Leu Arg Asp Asp Ser
    50                  55                  60

Ser Lys Glu Ile Ile Thr Val Phe Arg Gly Thr Gly Ser Asp Thr Asn
65                  70                  75                  80

Leu Gln Leu Asp Thr Asn Tyr Thr Leu Thr Pro Phe Asp Thr Leu Pro
                85                  90                  95

Gln Cys Asn Gly Cys Glu Val His Gly Gly Tyr Tyr Ile Gly Trp Val
            100                 105                 110

Ser Val Gln Asp Gln Val Glu Ser Leu Val Lys Gln Gln Val Ser Gln
        115                 120                 125

Tyr Pro Asp Tyr Ala Leu Thr Val Thr Gly His Ser Leu Gly Ala Ser
    130                 135                 140

Leu Ala Ala Leu Thr Ala Ala Gln Leu Ser Ala Thr Tyr Asp Asn Ile
145                 150                 155                 160

Arg Leu Tyr Thr Phe Gly Glu Pro Arg Ser Gly Asn Gln Ala Phe Ala
                165                 170                 175

Ser Tyr Met Asn Asp Ala Phe Gln Ala Ser Ser Pro Asp Thr Thr Gln
            180                 185                 190

Tyr Phe Arg Val Thr His Ala Asn Asp Gly Ile Pro Asn Leu Pro Pro
        195                 200                 205

Val Glu Gln Gly Tyr Ala His Gly Gly Val Glu Tyr Trp Ser Val Asp
    210                 215                 220

Pro Tyr Ser Ala Gln Asn Thr Phe Val Cys Thr Gly Asp Glu Val Gln
225                 230                 235                 240

Cys Cys Glu Ala Gln Gly Gly Gln Gly Val Asn Asn Ala His Thr Thr
                245                 250                 255

Tyr Phe Gly Met Thr Ser Gly Ala Cys Thr Trp
            260                 265

<210> SEQ ID NO 8
<211> LENGTH: 266
<212> TYPE: PRT
<213> ORGANISM: Aspergillus tubingensis

<400> SEQUENCE: 8

Thr Ala Gly His Ala Leu Ala Ala Ser Thr Gln Gly Ile Ser Glu Asp
1               5                   10                  15

Leu Tyr Ser Arg Leu Val Glu Met Ala Thr Ile Ser Gln Ala Ala Tyr
            20                  25                  30

Ala Asp Leu Cys Asn Ile Pro Ser Thr Ile Ile Lys Gly Glu Lys Ile
        35                  40                  45

Tyr Asn Ser Gln Thr Asp Ile Asn Gly Trp Ile Leu Arg Asp Asp Ser
    50                  55                  60

```
Ser Lys Glu Ile Ile Thr Val Phe Arg Gly Thr Gly Ser Asp Thr Asn
 65                  70                  75                  80

Leu Gln Leu Asp Thr Asn Tyr Thr Leu Thr Pro Phe Asp Thr Leu Pro
                 85                  90                  95

Gln Cys Asn Ser Cys Glu Val His Gly Gly Tyr Tyr Ile Gly Trp Ile
            100                 105                 110

Ser Val Gln Asp Gln Val Glu Ser Leu Val Gln Gln Val Ser Gln
        115                 120                 125

Phe Pro Asp Tyr Ala Leu Thr Val Thr Gly His Ser Leu Gly Ala Ser
130                 135                 140

Leu Ala Ala Leu Thr Ala Ala Gln Leu Ser Ala Thr Tyr Asp Asn Ile
145                 150                 155                 160

Arg Leu Tyr Thr Phe Gly Glu Pro Arg Ser Asn Gln Ala Phe Ala Ser
                165                 170                 175

Tyr Met Asn Asp Ala Phe Gln Ala Ser Ser Pro Asp Thr Thr Gln Tyr
            180                 185                 190

Phe Arg Val Thr His Ala Asn Asp Gly Ile Pro Asn Leu Pro Pro Ala
        195                 200                 205

Asp Glu Gly Tyr Ala His Gly Val Val Glu Tyr Trp Ser Val Asp Pro
210                 215                 220

Tyr Ser Ala Gln Asn Thr Phe Val Cys Thr Gly Asp Glu Val Gln Cys
225                 230                 235                 240

Cys Glu Ala Gln Gly Gly Gln Gly Val Asn Asn Ala His Thr Thr Tyr
                245                 250                 255

Phe Gly Met Thr Ser Gly His Cys Thr Trp
            260                 265

<210> SEQ ID NO 9
<211> LENGTH: 276
<212> TYPE: PRT
<213> ORGANISM: Fusarium oxysporum

<400> SEQUENCE: 9

Ala Val Gly Val Thr Thr Thr Asp Phe Ser Asn Phe Lys Phe Tyr Ile
 1               5                  10                  15

Gln His Gly Ala Ala Ala Tyr Cys Asn Ser Glu Ala Ala Ala Gly Ser
                20                  25                  30

Lys Ile Thr Cys Ser Asn Asn Gly Cys Pro Thr Val Gln Gly Asn Gly
            35                  40                  45

Ala Thr Ile Val Thr Ser Phe Val Gly Ser Lys Thr Gly Ile Gly Gly
        50                  55                  60

Tyr Val Ala Thr Asp Ser Ala Arg Lys Glu Ile Val Val Ser Phe Arg
 65                  70                  75                  80

Gly Ser Ile Asn Ile Arg Asn Trp Leu Thr Asn Leu Asp Phe Gly Gln
                 85                  90                  95

Glu Asp Cys Ser Leu Val Ser Gly Cys Gly Val His Ser Gly Phe Gln
            100                 105                 110

Arg Ala Trp Asn Glu Ile Ser Ser Gln Ala Thr Ala Ala Val Ala Ser
        115                 120                 125

Ala Arg Lys Ala Asn Pro Ser Phe Asn Val Ile Ser Thr Gly His Ser
130                 135                 140

Leu Gly Gly Ala Val Ala Val Leu Ala Ala Ala Asn Leu Arg Val Gly
145                 150                 155                 160

Gly Thr Pro Val Asp Ile Tyr Thr Tyr Gly Ser Pro Arg Val Gly Asn
                165                 170                 175
```

```
Ala Gln Leu Ser Ala Phe Val Ser Asn Gln Ala Gly Gly Glu Tyr Arg
            180                 185                 190

Val Thr His Ala Asp Asp Pro Val Pro Arg Leu Pro Leu Ile Phe
            195                 200                 205

Gly Tyr Arg His Thr Thr Pro Glu Phe Trp Leu Ser Gly Gly Gly
210                 215                 220

Asp Lys Val Asp Tyr Thr Ile Ser Asp Val Lys Val Cys Glu Gly Ala
225                 230                 235                 240

Ala Asn Leu Gly Cys Asn Gly Gly Thr Leu Gly Leu Asp Ile Ala Ala
            245                 250                 255

His Leu His Tyr Phe Gln Ala Thr Asp Ala Cys Asn Ala Gly Gly Phe
            260                 265                 270

Ser Trp Arg Arg
            275

<210> SEQ ID NO 10
<211> LENGTH: 273
<212> TYPE: PRT
<213> ORGANISM: Fusarium heterosporum

<400> SEQUENCE: 10

Thr Val Thr Thr Gln Asp Leu Ser Asn Phe Arg Phe Tyr Leu Gln His
1               5                   10                  15

Ala Asp Ala Ala Tyr Cys Asn Phe Asn Thr Ala Val Gly Lys Pro Val
            20                  25                  30

His Cys Ser Ala Gly Asn Cys Pro Asp Ile Glu Lys Asp Ala Ala Ile
        35                  40                  45

Val Val Gly Ser Val Gly Thr Lys Thr Gly Ile Gly Ala Tyr Val
    50                  55                  60

Ala Thr Asp Asn Ala Arg Lys Glu Ile Val Val Ser Val Arg Gly Ser
65              70                  75                  80

Ile Asn Val Arg Asn Trp Ile Thr Asn Phe Asn Phe Gly Gln Lys Thr
                85                  90                  95

Cys Asp Leu Val Ala Gly Cys Gly Val His Thr Gly Phe Leu Asp Ala
            100                 105                 110

Trp Glu Glu Val Ala Ala Asn Val Lys Ala Val Ser Ala Ala Lys
        115                 120                 125

Thr Ala Asn Pro Thr Phe Lys Phe Val Val Thr Gly His Ser Leu Gly
    130                 135                 140

Gly Ala Val Ala Thr Ile Ala Ala Ala Tyr Leu Arg Lys Asp Gly Phe
145                 150                 155                 160

Pro Phe Asp Leu Tyr Thr Tyr Gly Ser Pro Arg Val Gly Asn Asp Phe
                165                 170                 175

Phe Ala Asn Phe Val Thr Gln Gln Thr Gly Ala Glu Tyr Arg Val Thr
            180                 185                 190

His Gly Asp Asp Pro Val Pro Arg Leu Pro Ile Val Phe Gly Tyr
        195                 200                 205

Arg His Thr Ser Pro Glu Tyr Trp Leu Asn Gly Pro Leu Asp Lys
    210                 215                 220

Asp Tyr Thr Val Thr Glu Ile Lys Val Cys Glu Gly Ile Ala Asn Val
225                 230                 235                 240

Met Cys Asn Gly Gly Thr Ile Gly Leu Asp Ile Leu Ala His Ile Thr
                245                 250                 255

Tyr Phe Gln Ser Met Ala Thr Cys Ala Pro Ile Ala Ile Pro Trp Lys
            260                 265                 270
```

Arg

```
<210> SEQ ID NO 11
<211> LENGTH: 278
<212> TYPE: PRT
<213> ORGANISM: Aspergillus oryzae

<400> SEQUENCE: 11
```

| | | | | | | | | | | | | | | | |
|---|---|---|---|---|---|---|---|---|---|---|---|---|---|---|---|
| Asp | Ile | Pro | Thr | Thr | Gln | Leu | Glu | Asp | Phe | Lys | Phe | Trp | Val | Gln | Tyr |
| 1 | | | | 5 | | | | | 10 | | | | | 15 | |
| Ala | Ala | Ala | Thr | Tyr | Cys | Pro | Asn | Asn | Tyr | Val | Ala | Lys | Asp | Gly | Glu |
| | | | 20 | | | | | 25 | | | | | 30 | | |
| Lys | Leu | Asn | Cys | Ser | Val | Gly | Asn | Cys | Pro | Asp | Val | Glu | Ala | Ala | Gly |
| | | | 35 | | | | | 40 | | | | | 45 | | |
| Ser | Thr | Val | Lys | Leu | Ser | Phe | Ser | Asp | Asp | Thr | Ile | Thr | Asp | Thr | Ala |
| | 50 | | | | | 55 | | | | | 60 | | | | |
| Gly | Phe | Val | Ala | Val | Asp | Asn | Thr | Asn | Lys | Ala | Ile | Val | Val | Ala | Phe |
| 65 | | | | | 70 | | | | | 75 | | | | | 80 |
| Arg | Gly | Ser | Tyr | Ser | Ile | Arg | Asn | Trp | Val | Thr | Asp | Ala | Thr | Phe | Pro |
| | | | | 85 | | | | | 90 | | | | | 95 | |
| Gln | Thr | Asp | Pro | Gly | Leu | Cys | Asp | Gly | Cys | Lys | Ala | Glu | Leu | Gly | Phe |
| | | | 100 | | | | | 105 | | | | | 110 | | |
| Trp | Thr | Ala | Trp | Lys | Val | Val | Arg | Asp | Arg | Ile | Ile | Lys | Thr | Leu | Asp |
| | | | 115 | | | | | 120 | | | | | 125 | | |
| Glu | Leu | Lys | Pro | Glu | His | Ser | Asp | Tyr | Lys | Ile | Val | Val | Gly | His | |
| | 130 | | | | | 135 | | | | | 140 | | | | |
| Ser | Leu | Gly | Ala | Ala | Ile | Ala | Ser | Leu | Ala | Ala | Asp | Leu | Arg | Thr | |
| 145 | | | | | 150 | | | | | 155 | | | | | 160 |
| Lys | Asn | Tyr | Asp | Ala | Ile | Leu | Tyr | Ala | Tyr | Ala | Ala | Pro | Arg | Val | Ala |
| | | | | 165 | | | | | 170 | | | | | 175 | |
| Asn | Lys | Pro | Leu | Ala | Glu | Phe | Ile | Thr | Asn | Gln | Gly | Asn | Asn | Tyr | Arg |
| | | | 180 | | | | | 185 | | | | | 190 | | |
| Phe | Thr | His | Asn | Asp | Asp | Pro | Val | Pro | Lys | Leu | Pro | Leu | Leu | Thr | Met |
| | | | 195 | | | | | 200 | | | | | 205 | | |
| Gly | Tyr | Val | His | Ile | Ser | Pro | Glu | Tyr | Tyr | Ile | Thr | Ala | Pro | Asp | Asn |
| | 210 | | | | | 215 | | | | | 220 | | | | |
| Thr | Thr | Val | Thr | Asp | Asn | Gln | Val | Thr | Val | Leu | Asp | Gly | Tyr | Val | Asn |
| 225 | | | | | 230 | | | | | 235 | | | | | 240 |
| Phe | Lys | Gly | Asn | Thr | Gly | Thr | Ser | Gly | Gly | Leu | Pro | Asp | Leu | Leu | Ala |
| | | | | 245 | | | | | 250 | | | | | 255 | |
| Phe | His | Ser | His | Val | Trp | Tyr | Phe | Ile | His | Ala | Asp | Ala | Cys | Lys | Gly |
| | | | 260 | | | | | 265 | | | | | 270 | | |
| Pro | Gly | Leu | Pro | Leu | Arg | | | | | | | | | | |
| | | | 275 | | | | | | | | | | | | |

```
<210> SEQ ID NO 12
<211> LENGTH: 278
<212> TYPE: PRT
<213> ORGANISM: Penicillium camemberti

<400> SEQUENCE: 12
```

| | | | | | | | | | | | | | | | |
|---|---|---|---|---|---|---|---|---|---|---|---|---|---|---|---|
| Asp | Val | Ser | Thr | Ser | Glu | Leu | Asp | Gln | Phe | Glu | Phe | Trp | Val | Gln | Tyr |
| 1 | | | | 5 | | | | | 10 | | | | | 15 | |
| Ala | Ala | Ala | Ser | Tyr | Tyr | Glu | Ala | Asp | Tyr | Thr | Ala | Gln | Val | Gly | Asp |
| | | | 20 | | | | | 25 | | | | | 30 | | |
| Lys | Leu | Ser | Cys | Ser | Lys | Gly | Asn | Cys | Pro | Glu | Val | Glu | Ala | Thr | Gly |
| | | | 35 | | | | | 40 | | | | | 45 | | |

Ala Thr Val Ser Tyr Asp Phe Ser Asp Ser Thr Ile Thr Asp Thr Ala
            50                  55                  60

Gly Tyr Ile Ala Val Asp His Thr Asn Ser Ala Val Val Leu Ala Phe
65                  70                  75                  80

Arg Gly Ser Tyr Ser Val Arg Asn Trp Val Ala Asp Ala Thr Phe Val
                85                  90                  95

His Thr Asn Pro Gly Leu Cys Asp Gly Cys Leu Ala Glu Leu Gly Phe
            100                 105                 110

Trp Ser Ser Trp Lys Leu Val Arg Asp Asp Ile Ile Lys Glu Leu Lys
            115                 120                 125

Glu Val Val Ala Gln Asn Pro Asn Tyr Glu Leu Val Val Gly His
            130                 135                 140

Ser Leu Gly Ala Ala Val Ala Thr Leu Ala Ala Thr Asp Leu Arg Gly
145                 150                 155                 160

Lys Gly Tyr Pro Ser Ala Lys Leu Tyr Ala Tyr Ala Ser Pro Arg Val
                165                 170                 175

Gly Asn Ala Ala Leu Ala Lys Tyr Ile Thr Ala Gln Gly Asn Asn Phe
            180                 185                 190

Arg Phe Thr His Thr Asn Asp Pro Val Pro Lys Leu Pro Leu Leu Ser
            195                 200                 205

Met Gly Tyr Val His Val Ser Pro Glu Tyr Trp Ile Thr Ser Pro Asn
210                 215                 220

Asn Ala Thr Val Ser Thr Ser Asp Ile Lys Val Ile Asp Gly Asp Val
225                 230                 235                 240

Ser Phe Asp Gly Asn Thr Gly Thr Gly Leu Pro Leu Leu Thr Asp Phe
                245                 250                 255

Glu Ala His Ile Trp Tyr Phe Val Gln Val Asp Ala Gly Lys Gly Pro
            260                 265                 270

Gly Leu Pro Phe Lys Arg
        275

<210> SEQ ID NO 13
<211> LENGTH: 270
<212> TYPE: PRT
<213> ORGANISM: Aspergillus foetidus

<400> SEQUENCE: 13

Ser Val Ser Thr Ser Thr Leu Asp Glu Leu Gln Leu Phe Ala Gln Trp
1               5                   10                  15

Ser Ala Ala Ala Tyr Cys Ser Asn Asn Ile Asp Ser Lys Asp Ser Asn
                20                  25                  30

Leu Thr Cys Thr Ala Asn Ala Cys Pro Ser Val Glu Glu Ala Ser Thr
            35                  40                  45

Thr Met Leu Leu Glu Phe Asp Leu Thr Asn Asp Phe Gly Gly Thr Ala
            50                  55                  60

Gly Phe Leu Ala Ala Asp Asn Thr Asn Lys Arg Leu Val Val Ala Phe
65                  70                  75                  80

Arg Gly Ser Ser Thr Ile Glu Asn Trp Ile Ala Asn Leu Asp Phe Ile
                85                  90                  95

Leu Glu Asp Asn Asp Asp Leu Cys Thr Gly Cys Lys Val His Thr Gly
            100                 105                 110

Phe Trp Lys Ala Trp Glu Ser Ala Ala Asp Glu Leu Thr Ser Lys Ile
            115                 120                 125

Lys Ser Ala Met Ser Thr Tyr Ser Gly Tyr Thr Leu Tyr Phe Thr Gly
        130                 135                 140

```
His Ser Leu Gly Gly Ala Leu Ala Thr Leu Gly Ala Thr Val Leu Arg
145                 150                 155                 160

Asn Asp Gly Tyr Ser Val Glu Leu Tyr Thr Tyr Gly Cys Pro Arg Ile
            165                 170                 175

Gly Asn Tyr Ala Leu Ala Glu His Ile Thr Ser Gln Gly Ser Gly Ala
        180                 185                 190

Asn Phe Arg Val Thr His Leu Asn Asp Ile Val Pro Arg Val Pro Pro
    195                 200                 205

Met Asp Phe Gly Phe Ser Gln Pro Ser Pro Glu Tyr Trp Ile Thr Ser
210                 215                 220

Gly Asn Gly Ala Ser Val Thr Ala Ser Asp Ile Glu Val Ile Glu Gly
225                 230                 235                 240

Ile Asn Ser Thr Ala Gly Asn Ala Gly Glu Ala Thr Val Ser Val Leu
                245                 250                 255

Ala His Leu Trp Tyr Phe Phe Ala Ile Ser Glu Cys Leu Leu
            260                 265                 270
```

<210> SEQ ID NO 14
<211> LENGTH: 270
<212> TYPE: PRT
<213> ORGANISM: Aspergillus niger

<400> SEQUENCE: 14

```
Ser Val Ser Thr Ser Thr Leu Asp Glu Leu Gln Leu Phe Ser Gln Trp
1               5                   10                  15

Ser Ala Ala Ala Tyr Cys Ser Asn Asn Ile Asp Ser Asp Asp Ser Asn
            20                  25                  30

Val Thr Cys Thr Ala Asp Ala Cys Pro Ser Val Glu Glu Ala Ser Thr
        35                  40                  45

Lys Met Leu Leu Glu Phe Asp Leu Thr Asn Asn Phe Gly Gly Thr Ala
    50                  55                  60

Gly Phe Leu Ala Ala Asp Asn Thr Asn Lys Arg Leu Val Val Ala Phe
65                  70                  75                  80

Arg Gly Ser Ser Thr Ile Lys Asn Trp Ile Ala Asp Leu Asp Phe Ile
                85                  90                  95

Leu Gln Asp Asn Asp Asp Leu Cys Thr Gly Cys Lys Val His Thr Gly
            100                 105                 110

Phe Trp Lys Ala Trp Glu Ala Ala Ala Asp Asn Leu Thr Ser Lys Ile
        115                 120                 125

Lys Ser Ala Met Ser Thr Tyr Ser Gly Tyr Thr Leu Tyr Phe Thr Gly
    130                 135                 140

His Ser Leu Gly Gly Ala Leu Ala Thr Leu Gly Ala Thr Val Leu Arg
145                 150                 155                 160

Asn Asp Gly Tyr Ser Val Glu Leu Tyr Thr Tyr Gly Cys Pro Arg Val
            165                 170                 175

Gly Asn Tyr Ala Leu Ala Glu His Ile Thr Ser Gln Gly Ser Gly Ala
        180                 185                 190

Asn Phe Pro Val Thr His Leu Asn Asp Ile Val Pro Arg Val Pro Pro
    195                 200                 205

Met Asp Phe Gly Phe Ser Gln Pro Ser Pro Glu Tyr Trp Ile Thr Ser
210                 215                 220

Gly Thr Gly Ala Ser Val Thr Ala Ser Asp Ile Glu Leu Ile Glu Gly
225                 230                 235                 240

Ile Asn Ser Thr Ala Gly Asn Ala Gly Glu Ala Thr Val Asp Val Leu
                245                 250                 255
```

```
Ala His Leu Trp Tyr Phe Phe Ala Ile Ser Glu Cys Leu Leu
        260                 265                 270

<210> SEQ ID NO 15
<211> LENGTH: 269
<212> TYPE: PRT
<213> ORGANISM: Aspergillus oryzae

<400> SEQUENCE: 15

Asp Val Ser Ser Leu Leu Asn Asn Leu Asp Leu Phe Ala Gln Tyr
1               5                   10                  15

Ser Ala Ala Tyr Cys Asp Glu Asn Leu Asn Ser Thr Gly Thr Lys
            20                  25                  30

Leu Thr Cys Ser Val Gly Asn Cys Pro Leu Val Glu Ala Ala Ser Thr
        35                  40                  45

Gln Ser Leu Asp Glu Phe Asn Glu Ser Ser Tyr Gly Asn Pro Ala
    50                  55                  60

Gly Tyr Leu Ala Ala Asp Glu Thr Asn Lys Leu Leu Val Leu Ser Phe
65                  70                  75                  80

Arg Gly Ser Ala Asp Leu Ala Asn Trp Val Ala Asn Leu Asn Phe Gly
                85                  90                  95

Leu Glu Asp Ala Ser Asp Leu Cys Ser Gly Cys Glu Val His Ser Gly
            100                 105                 110

Phe Trp Lys Ala Trp Ser Glu Ile Ala Asp Thr Ile Thr Ser Lys Val
        115                 120                 125

Glu Ser Ala Leu Ser Asp His Ser Asp Tyr Ser Leu Val Leu Thr Gly
130                 135                 140

His Ser Tyr Gly Ala Ala Leu Ala Ala Leu Ala Ala Thr Ala Leu Arg
145                 150                 155                 160

Asn Ser Gly His Ser Val Glu Leu Tyr Asn Tyr Gly Gln Pro Arg Leu
                165                 170                 175

Gly Asn Glu Ala Leu Ala Thr Tyr Ile Thr Asp Gln Asn Lys Gly Gly
            180                 185                 190

Asn Tyr Arg Val Thr His Thr Asn Asp Ile Val Pro Lys Leu Pro Pro
        195                 200                 205

Thr Leu Leu Gly Tyr His His Phe Ser Pro Glu Tyr Tyr Ile Ser Ser
    210                 215                 220

Ala Asp Glu Ala Thr Val Thr Thr Thr Asp Val Thr Glu Val Thr Gly
225                 230                 235                 240

Ile Asp Ala Thr Gly Gly Asn Asp Gly Thr Asp Gly Thr Ser Ile Asp
                245                 250                 255

Ala His Arg Trp Tyr Phe Ile Tyr Ile Ser Glu Cys Ser
            260                 265

<210> SEQ ID NO 16
<211> LENGTH: 251
<212> TYPE: PRT
<213> ORGANISM: Landerina penisapora

<400> SEQUENCE: 16

Pro Gln Asp Ala Tyr Thr Ala Ser His Ala Asp Leu Val Lys Tyr Ala
1               5                   10                  15

Thr Tyr Ala Gly Leu Ala Tyr Gln Thr Thr Asp Ala Trp Pro Ala Ser
            20                  25                  30

Arg Thr Val Pro Lys Asp Thr Leu Ile Ser Ser Phe Asp His Thr
        35                  40                  45
```

```
Leu Lys Gly Ser Ser Gly Tyr Ile Ala Phe Asn Glu Pro Cys Lys Glu
    50                  55                  60

Ile Ile Val Ala Tyr Arg Gly Thr Asp Ser Leu Ile Asp Trp Leu Thr
65                  70                  75                  80

Asn Leu Asn Phe Asp Lys Thr Ala Trp Pro Ala Asn Ile Ser Asn Ser
                85                  90                  95

Leu Val His Glu Gly Phe Leu Asn Ala Tyr Leu Val Ser Met Gln Gln
            100                 105                 110

Val Gln Glu Ala Val Asp Ser Leu Leu Ala Lys Cys Pro Asp Ala Thr
        115                 120                 125

Ile Ser Phe Thr Gly His Ser Leu Gly Gly Ala Leu Ala Cys Ile Ser
    130                 135                 140

Met Val Asp Thr Ala Gln Arg His Arg Gly Ile Lys Met Gln Met Phe
145                 150                 155                 160

Thr Tyr Gly Gln Pro Arg Thr Gly Asn Gln Ala Phe Ala Glu Tyr Val
                165                 170                 175

Glu Asn Leu Gly His Pro Val Phe Arg Val Val Tyr Arg His Asp Ile
            180                 185                 190

Val Pro Arg Met Pro Pro Met Asp Leu Gly Phe Gln His His Gly Gln
        195                 200                 205

Glu Val Trp Tyr Glu Gly Asp Glu Asn Ile Lys Phe Cys Lys Gly Glu
    210                 215                 220

Gly Glu Asn Leu Thr Cys Glu Leu Gly Val Pro Phe Ser Glu Leu Asn
225                 230                 235                 240

Ala Lys Asp His Ser Glu Tyr Pro Gly Met His
                245                 250

<210> SEQ ID NO 17
<211> LENGTH: 12
<212> TYPE: PRT
<213> ORGANISM: Artificial Sequence
<220> FEATURE:
<223> OTHER INFORMATION: Synthetic construct

<400> SEQUENCE: 17

Ala Cys Met Ser His Thr Trp Gly Glu Arg Asn Leu
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic construct

<400> SEQUENCE: 18

His Gly Trp Gly Glu Asp Ala Asn Leu Ala Met Asn Pro Ser
1               5                   10
```